(12) United States Patent
Konishi et al.

(10) Patent No.: US 9,365,603 B2
(45) Date of Patent: *Jun. 14, 2016

(54) METHOD FOR PRODUCING MYO-INOSITOL AND MYO-INOSITOL DERIVATIVE

(71) Applicant: Asahi Kasei Chemicals Corporation, Tokyo (JP)

(72) Inventors: Kazunobu Konishi, Tokyo (JP); Shinichi Imazu, Tokyo (JP); Mayumi Sato, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/343,585

(22) PCT Filed: Nov. 9, 2012

(86) PCT No.: PCT/JP2012/079182
§ 371 (c)(1),
(2) Date: Mar. 7, 2014

(87) PCT Pub. No.: WO2013/073483
PCT Pub. Date: May 23, 2013

(65) Prior Publication Data
US 2014/0296497 A1    Oct. 2, 2014

(30) Foreign Application Priority Data
Nov. 14, 2011  (JP) ................... 2011-248438

(51) Int. Cl.
| | | |
|---|---|---|
| C12P 19/46 | (2006.01) |
| C07H 15/207 | (2006.01) |
| C12N 15/70 | (2006.01) |
| C12P 7/02 | (2006.01) |
| C12N 9/16 | (2006.01) |

(52) U.S. Cl.
CPC .............. *C07H 15/207* (2013.01); *C12N 9/16* (2013.01); *C12N 15/70* (2013.01); *C12P 7/02* (2013.01); *C12P 19/46* (2013.01); *Y02P 20/52* (2015.11)

(58) Field of Classification Search
CPC .......... C12P 19/46; C12P 7/02; C12N 15/70; C12N 9/16; C07H 15/207; Y02P 20/52
USPC ................. 536/4.1; 435/252.33, 79
See application file for complete search history.

(56) References Cited

U.S. PATENT DOCUMENTS

| 2004/0209337 A1 | 10/2004 | Frost et al. |
| 2011/0124063 A1 | 5/2011 | Lynch |

FOREIGN PATENT DOCUMENTS

| JP | 08-000258 | 1/1996 |
| JP | 08-038188 | 2/1996 |
| JP | 08-089262 | 4/1996 |
| JP | 09-117295 | 5/1997 |
| JP | 09-220093 | 8/1997 |
| JP | 10-042860 | 2/1998 |
| JP | 10-042882 | 2/1998 |
| JP | 10-042883 | 2/1998 |
| JP | 10-271995 | 10/1998 |
| JP | 2000-41689 | 2/2000 |
| JP | 2011-55722 | 3/2011 |
| KR | 10-2001-0111577 A | 12/2001 |
| WO | 00/56911 A1 | 9/2000 |
| WO | 2009/145838 | 12/2009 |
| WO | 2011/063304 | 5/2011 |

OTHER PUBLICATIONS

Office Action issued in counterpart Taiwanese Patent Application No. 1032099383001 dated Jul. 22, 2014.
Yamamoto et al., "Acceptor Recognition of Kojibiose Phosphorylase from Thermoanaerobacter brockii: Syntheses of Glycosyl Glycerol and myo-Inositol," Journal of Bioscience and Bioengineering, 101: 427-433 (2006).
Gorin et al., "Formation of O-Beta-D-glucopyranosyl- and O-Beta-D-galactopyranosyl-myo-inositols by glycosyl transfer," Canadian Journal of Chemistry, 43(8): 2259-2264 (1965).
Hansen et al., "Synthesis of 1,2,3,4-Tetrahydroxybenzene from D-Glucose: Exploiting myo-Inositol as a Precursor to Aromatic Chemicals," J. Am. Chem. Soc., 121: 3799-3800 (1999).
Hopf et al, "O-Beta-D-Glucopyranosyl-(1-1)-Myo-Inositol(Glucinol) in higher plants," Zeitschrift fuer Pflanzenphysiologie, 100(3): 189-195 (1980).
Sato et al., "Synthesis of glucosyl-inositol using a CGTase, isolation and characterization of the positional isomers, and assimilation profiles for intestinal bacteria," Biotechnology Letters, 14(8): 659-664 (1992).
Watanabe et al., "Absolute configuration of 4-alpha-D-glucopyranosyl-myo-inositol, enzymatic transglycosylation product," Journal of Carbohydrate Chemistry, 12(6): 685-692 (1993).
International Search Report issued in a corresponding International Patent Application No. PCT/JP2012/079182, mailed Jan. 22, 2013.
Office Action issued in counterpart Chinese Patent Application No. 201280050798 dated Jul. 3, 2015.
Office Action issued in counterpart Korean Patent Application No. 10-2014-7007118 dated Feb. 24, 2016.

*Primary Examiner* — Clinton Brooks
*Assistant Examiner* — Yih-Horng Shiao
(74) *Attorney, Agent, or Firm* — Morgan, Lewis & Bockius LLP

(57) ABSTRACT

[Problem] To impart significantly improved myo-inositol producing capability, suitable for use in recombinant DNA techniques and synthetic biology methods, to a host microorganism that does not possess an endogenous myo-inositol biosynthesis pathway, such as *Escherichia coli*. [Solution] Inositol monophosphatase activity is strengthened in a transformant obtained by introducing a myo-inositol biosynthesis pathway into a host microorganism that does not possess an endogenous myo-inositol biosynthesis pathway.

7 Claims, 6 Drawing Sheets

FIG. 1 atgacagaag ataatattgc tccaatcacc tccgttaaag tagttaccga caagtgcacg
tacaaggaca acgagctgct caccaagtac agctacgaaa atgctgtagt tacgaagaca
gctagtggcc gcttcgatgt cacgcccact gttcaagact acgtgttcaa acttgactta
aaaaagccgg aaaaactagg aattatgctc attgggttag gtggcaacaa tggctccacc
ttagtggcct cggtattggc gaataagcac aatgtggagt ttcaaactaa ggaaggcgtt
aagcaaccaa actacttcgg ctccatgact caatgttcta ccttgaaact gggtgtcgat
gcggagggga atgacgttta tgctcctttt aactctctgt tgcccatggt tagcccaaac
gactttgtcg tctctggttg ggacatcaat aacgcagatc tatacgaagc tatgcagaga
agtcaggttc tcgaatatga tctgcaacaa cgcttgaagg cgaagatgtc cttggtgaag
cctcttcctt ccatttacta ccctgatttc attgcagcta atcaagatga gagagccaat
aactgcatca atttggatga aaaaggcaac gtaaccacga ggggtaagtg ggcccatctg
caacgcatca gacgcgatat tcagaatttc aaagaagaaa acgcccttga taaagtaatc
gttctttgga ctgcaaatac tgagaggtac gtagaagtat ctcctggtgt taatgacacc
atggaaaacc tcttgcagtc tattaagaat gaccatgaag agattgctcc ttccacgatc
tttgcagcag catctatctt ggaaggtgtc ccctatatta atggttcacc gcagaatact
tttgttcccg gcttggttca gctggctgag catgagggta cattcattgc gggagacgat
ctcaagtcgg gacaaaccaa gttgaagtct gttctggccc agttcttagt ggatgcaggt
attaaaccgg tctccattgc atcctataac catttaggca ataatgacgg ttataactta
tctgctccaa aacaatttag gtctaaggag atttccaaaa gttctgtcat agatgacatc
atcgcgtcta atgatatctt gtacaatgat aaactgggta aaaaagttga ccactgcatt
gtcattaaat atatgaagcc cgtcggggac tcaaaagtgg caatggacga gtattacagt
gagttgatgt taggtggcca taaccggatt tccattcaca atgtttgcga agattcttta
ctggctacgc ccttgatcat cgatctttta gtcatgactg agttttgtac aagagtgtcc
tataagaagg tggacccagt taagaagat gctggcaaat tgagaactt ttatccagtt
ttaaccttct tgagttactg gttaaaagct ccattaacaa gaccaggatt tcacccggtg
aatggcttaa acaagcaaag aaccgcctta gaaattttt taagattgtt gattggattg
ccttctcaaa acgaactaag attcgaagag agattgttgt aa (SEQ ID NO 1)

FIG. 2 atgcatccgatgctgaacatcgccgtgcgcgcagcgcgcaaggcgggtaatttaattgcc
aaaaactatgaaacccgacgctgtagaagcgagccagaaaggcagtaacgatttcgtg
accaacgtagataaagctgccgaagcggtgattatcgacacgattcgtaaatcttaccca
cagcacaccatcatcaccgaagaaagcggtgaacttgaaggtactgatcaggatgttcaa
tgggttatcgatccactggatggcactaccaactttatcaaacgtctgccgcacttcgcg
gtatctatcgctgttcgtatcaaaggccgcaccgaagttgctgtggtatacgatcctatg
cgtaacgaactgttcaccgccactcgcggtcagggcgcacagctgaacggctaccgactg
cgcggcagcaccgctcgcgatctcgacggtactattctggcgaccggcttcccgttcaaa
gcaaaacagtacgccactacctacatcaacatcgtcggcaaactgttcaacgaatgtgca
gacttccgtcgtaccggttctgcggcgctggatctggcttacgtcgctgcgggtcgtgtt
gacggtttctttgaaatcggtctgcgcccgtgggacttcgccgcaggcgagctgctggtt
cgtgaagcgggcggcatcgtcagcgacttcaccggtggtcataactacatgctgaccggt
aacatcgttgctggtaaccgcgcgttgttaaagccatgctggcgaacatggtgacgag
ttaagcgacgctctgaagcgttaa (SEQ ID NO 3)

A) BEFORE REACTION; B) AFTER 3 HOURS OF REACTION; C) AFTER 22 HOURS OF REACTION

1) GLUCOSE; 2) MYO-INOSITOL; 3) MYO-INOSITOL DERIVATIVE

METHOD FOR PRODUCING MYO-INOSITOL AND MYO-INOSITOL DERIVATIVE

Sequence Listing Submission via EFS-Web

A computer readable text file, entitled "102771-5002_SequenceListing.txt," created on or about 28 Feb. 2014, with a file size of about 21 kb contains the sequence listing for this application and is hereby incorporated by reference in its entirety.

TECHNICAL FIELD

The present invention relates to application of gene recombination technology in production of myo-inositol. In particular, it relates to a method for industrial production of myo-inositol that utilizes transformants of prokaryotic microorganisms. The invention also relates to a novel myo-inositol derivative and a method for producing it.

BACKGROUND ART

Myo-inositol has been widely utilized as a component of nutritional foods, feeds, pharmaceuticals, and the like since it is an essential substance for many higher animals. For example, myo-inositol is known to play an important role in metabolism of fats and cholesterols and is held to be effective in prevention and treatment of hypercholesterolemia and the like. Many improvements of industrial-scale production processes for myo-inositol have therefore been proposed.

In the past, myo-inositol was extracted directly from rice bran, corn steep liquor, and the like. In addition to giving a low yield of myo-inositol, the extraction method produces many impurities, making purification of myo-inositol difficult and leading to very low production efficiency. Consequently, a method for producing myo-inositol from the culture obtained by culturing *Saccharomyces cerevisiae* having the ability to produce myo-inositol was also proposed. Nonetheless, this method was not implemented on an industrial scale as the productivity was still low and the method was not economically viable.

Microorganisms that can produce inositol more efficiently have therefore been sought. Patent Reference 1 discloses the discovery of yeast of the genus *Candida* capable of secreting inositol extracellularly and the utilization thereof. Patent References 2 and 3 disclose introduction of mutations to impart resistance to glucose antimetabolites and antibiotics, respectively, into the above yeast of the genus *Candida*. Patent References 4, 5, and 6 disclose improving the yield of inositol by introducing mutations to impart resistance to tertiary amines, hexachlorocyclohexane, and cetyl trimethylammonium salt, respectively, into yeasts of the genus *Candida* having the ability to produce inositol. Patent Reference 7 similarly discloses introduction of a mutation to impart resistance to 6-halogeno-6-deoxyglucose into yeast of the genus *Candida* having the ability to produce inositol. Patent Reference 8 also discloses introduction of a mutation to impart resistance to halogenated pyruvic acid into yeast of the genus *Candida* having the ability to produce inositol.

The prior art also describes transformation of yeast by gene recombination. Patent Reference 9 discloses that it is possible to impart the ability to produce inositol to yeast by transforming yeast of the genus *Candida* that does not have the ability to secrete inositol by inositol-1-phosphate synthase-encoding DNA alone, based on the reasonable inference that inositol-1-phosphate synthase is responsible for a rate-limiting reaction in the series of myo-inositol biosynthetic reactions. Patent Reference 10 discloses that the inositol productivity of yeast is improved by introducing inositol-1-phosphate synthase-encoding DNA alone into yeast under the control of a glycerol-3-phosphate dehydrogenase gene promoter.

Patent Reference 11 relates to inositol production by methanol-assimilating yeast *Pichia pastoris*, and it discloses introduction of an inositol phosphate phosphatase gene simultaneously with introduction of a myo-inositol-1-phosphate synthase gene into this yeast. However, the significance and effect of the additional introduction of an inositol phosphate phosphatase gene are not revealed.

Therefore, all of the above references relating to yeasts presuppose that inositol-1-phosphate synthase is responsible for a rate-limiting reaction in the series of myo-inositol biosynthetic reactions and do not suggest the importance of other enzymes that are present in the myo-inositol biosynthetic pathway.

On the other hand, prokaryotic microorganisms typified by *Escherichia coli* are extremely attractive organisms for industrial production as compared to yeasts due to strong proliferative capacity and various superiorities in fermentation control. However, no prokaryotic microorganism having an endogenous myo-inositol biosynthetic pathway is known.

Therefore, for the production of myo-inositol in an industrial scale by prokaryotic microorganisms, it is essential to construct an exogenous biosynthetic pathway within a prokaryotic microbial host.

Specifically, the following catalytic activities are necessary to construct a functional myo-inositol biosynthetic pathway within a prokaryotic microbial host:

activity 1: an activity to produce glucose-6-phosphate from a suitable carbon source;

activity 2: an activity to convert glucose-6-phosphate into myo-inositol-1-phosphate, that is, inositol-1-phosphate synthase activity; and activity 3: a phosphatase activity utilizing myo-inositol-1-phosphate as a substrate.

However, since glucose-6-phosphate that is a product of activity 1 is a metabolic intermediate universally produced by prokaryotic microorganisms, it is not essential to impart this activity to prokaryotic microorganisms. With regard to activity 3 as well, as far as the inventors know, the majority of prokaryotic microbial host cells that are suited to industrial production by conventional gene recombination techniques express endogenous inositol monophosphatase, or they have general monophosphatase activity capable of using myo-inositol-1-phosphate as a substrate. On the other hand, as for activity 2, there are many examples of prokaryotic microorganisms that do not have an inositol-1-phosphate synthase gene. Inositol-1-phosphate synthase is believed to be responsible for a rate-limiting reaction in myo-inositol biosynthetic reactions, as was mentioned above. Therefore, the introduction of an inositol-1-phosphate synthase gene into the cell has been thought to be necessary and sufficient to construct a functional myo-inositol biosynthetic pathway within a prokaryotic microbial host.

In fact, Non-patent Reference 1 discloses myo-inositol production within *E. coli* transformants, but only an inositol-1-phosphate synthase gene is introduced into these transformants.

Patent Reference 12 also discloses that only an inositol-1-phosphate synthase gene is introduced into an *E. coli* host cell to produce transformants thereby constructing an exogenous myo-inositol biosynthetic pathway within the transformants. However, the final target product in this reference is D-glucaric acid; myo-inositol is produced as an intermediate. It is noteworthy that this reference also states: "It should also be noted that we did not overexpress the suhB gene or a homologous phosphatase. However, no myo-inositol-1-phosphate was detected among the culture products, while myo-inositol did accumulate. Therefore, we conclude that the phosphatase activity is not limiting flux through the pathway" (page 33, lines 2-5).

Therefore, the prior art neither discloses nor suggests a critical role for inositol monophosphatase in myo-inositol production by recombinant microorganisms.

PRIOR ART REFERENCES

Patent References

Patent Reference 1: JP Kokai 8-00258
Patent Reference 2: JP Kokai 8-38188
Patent Reference 3: JP Kokai 8-89262
Patent Reference 4: JP Kokai 9-117295
Patent Reference 5: JP Kokai 10-42860
Patent Reference 6: JP Kokai 10-42882
Patent Reference 7: JP Kokai 10-42883
Patent Reference 8: JP Kokai 2000-41689
Patent Reference 9: JP Kokai 9-220093
Patent Reference 10: JP Kokai 10-271995
Patent Reference 11: JP Kokai 2011-55722
Patent Reference 12: WO2009/145838 pamphlet Non-Patent References Non-patent Reference 1: J. Am. Chem. Soc. 1999, Vol. 121, 3799-3800

SUMMARY OF THE INVENTION

Problems to be Solved by the Invention

Microorganisms that do not possess the endogenous myo-inositol biosynthetic pathway have the advantage of allowing easy control of myo-inositol productivity through the use of synthetic biology techniques in conjunction with gene recombination techniques. In particular, prokaryotic microbial hosts such as *E. coli* make the application of synthetic biology techniques even easier since they do not have an endogenous myo-inositol biosynthetic pathway and also do not have the inositol assimilation capacity (decomposition capacity) that many yeasts do. Its rapid growth capacity and ease of fermentation control make *E. coli* extremely attractive from the viewpoint of industrial fermentative production, and *E. coli* also has advantages from the viewpoint of the practical accomplishment in the application of gene recombination techniques and the established safety.

Therefore, the problem to be solved by the present invention is to impart a significantly improved ability to produce myo-inositol and related derivatives to host microorganisms that do not have an endogenous myo-inositol biosynthetic pathway.

Means Used to Solve the Above-Mentioned Problems

As was mentioned above, all of the research up to this point has suggested that inositol-1-phosphate synthase is responsible for a rate-limiting reaction in the myo-inositol biosynthetic reactions. In addition, none of the research has paid specific attention to inositol monophosphatase activity.

However, the inventors discovered that, surprisingly enough, inositol monophosphatase activity plays an important role in transformants obtained by introducing a myo-inositol biosynthetic pathway into a host microbe that does not have an endogenous myo-inositol biosynthetic pathway. The myo-inositol production capacity of such transformants was unexpectedly greatly improved by enhancing the inositol monophosphatase activity. The inventors also discovered a novel myo-inositol derivative in the cultures of such transformants.

Therefore, the first aspect of the present invention is (1) a method for producing myo-inositol or a myo-inositol derivative including the following steps:

1) a step of preparing a transformant of a microorganism that does not express endogenous inositol-1-phosphate synthase, the transformant containing at least an inositol-1-phosphate synthase-encoding exogenous gene introduced expressibly into the transformant, and the transformant having a gene recombination or mutation to induce overproduction of functional inositol monophosphatase or activation of inositol monophosphatase within the transformant; and 2) a step of bringing the transformant into contact with a carbon source that can be converted into myo-inositol by the transformant under conditions suited to growth and/or maintenance of the transformant.

More specifically, it is a method for producing myo-inositol or a myo-inositol derivative using a transformant having an inositol-1-phosphate synthase-encoding exogenous gene introduced expressibly into a microorganism that does not express endogenous inositol-1-phosphate synthase, the production method being characterized in that the transformant is a transformant having a gene recombination or mutation to induce the overproduction of functional inositol monophosphatase or the activation of inositol monophosphatase.

The myo-inositol derivative produced in the culture of (1) above is a novel compound; glucose and myo-inositol are β1→4 bonded in this derivative. Therefore, one embodiment of the present invention is:

(2) the production method according to (1) above, wherein the myo-inositol derivative is a compound represented by the following structural formula:

[Chemical Formula 1]

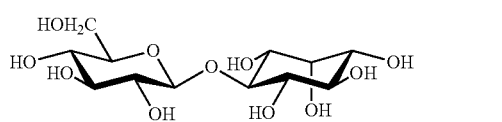

The advantages of prokaryotic microorganisms, especially *E. coli*, in the application of synthetic biology techniques and fermentative production have already been mentioned. Therefore, preferred embodiments of the present invention are: (3) the production method according to (1) or (2) above, wherein the microorganism that does not express endogenous inositol-1-phosphate synthase is a prokaryote;

(4) the production method according to any of (1) to (3) above, wherein the microorganism that does not express endogenous inositol-1-phosphate synthase is a microorganism having an endogenous inositol monophosphatase gene;

(5) the production method according to any of (1) to (4) above, wherein the microorganism that does not express endogenous inositol-1-phosphate synthase is a bacterium selected from the group consisting of *Escherichia coli*, bacteria belonging to the genus *Bacillus*, bacteria belonging to the genus *Corynebacterium*, and bacteria belonging to the genus *Zymomonas*; and (6) the production method according to (5) above, wherein the bacterium is *Escherichia coli*.

Regardless of whether or not the host microorganism has endogenous inositol monophosphatase activity, inducing overproduction of inositol monophosphatase within the cell can enhance the inositol monophosphatase activity of the cell. The overproduction of inositol monophosphatase can be induced in the cell by applying various known techniques. Therefore, the present invention includes the following embodiments:

(7) the production method according to any of (1) to (6) above, wherein the overproduction of inositol monophosphatase is induced by, in the microorganism, a) introducing an exogenous inositol monophosphatase gene, b) increasing the number of copies of an endogenous inositol monophosphatase gene, c) introducing a mutation into a regulatory region of the endogenous inositol monophosphatase gene, d) substituting the regulatory region of an endogenous inositol monophosphatase gene with a high expression-inducing exogenous regulatory region, or e) deleting the regulatory region of an endogenous inositol monophosphatase gene; and (8) the method according to (7) above, wherein the overproduction of inositol monophosphatase is induced by introducing the exogenous inositol monophosphatase gene into the above microorganism.

In addition, when the host cell has the endogenous inositol monophosphatase gene, the inositol monophosphatase activity of the cell can be enhanced by the following embodiments as well.

(9) The production method according to any of (1) to (6) above, wherein the activation of inositol monophosphatase is induced by, in the microorganism, f) introducing a mutation into an endogenous inositol monophosphatase gene, g) substituting all or part of the endogenous inositol monophosphatase gene, h) deleting part of the endogenous inositol monophosphatase gene, i) decreasing other proteins that lower inositol monophosphatase activity, or j) decreasing production of compounds that lower the inositol monophosphatase activity.

It is preferable to use a carbon source containing a compound suited to the production of glucose-6-phosphate, which is a substrate of inositol-1-phosphate synthase, as a culture base material in the fermentative production of myo-inositol of the present invention. Furthermore, the production method of the present invention may include an additional step of separating myo-inositol or a myo-inositol derivative from the culture of the transformant that has been grown and/or maintained in contact with the carbon source. Therefore, additional preferred embodiments of the present invention includes:

(10) the production method according to any of (1) to (9) above, wherein the carbon source contains a compound that can be converted into glucose-6-phosphate within the transformant;

(11) the production method according to (10) above, wherein the carbon source is one or more selected from the group consisting of D-glucose, sucrose, oligosaccharide, polysaccharide, starch, cellulose, rice bran, molasses, and biomass containing D-glucose; and

(12) the production method according to any of (1) to (11) above, further including a step of separating myo-inositol or a myo-inositol derivative amassed in a culture of the transformant grown and/or maintained in contact with the carbon source.

The present invention also intends transformants for use in the method for producing myo-inositol. Therefore, the second aspect of the present invention is:

(13) a transformant of a microorganism that does not express endogenous inositol-1-phosphate synthase, the transformant containing at least an inositol-1-phosphate synthase-encoding exogenous gene introduced expressibly into the transformant, and the transformant having a gene recombination or mutation to induce overproduction of functional inositol monophosphatase or activation of inositol monophosphatase within the transformant.

More specifically, it is a transformant having an inositol-1-phosphate synthase-encoding exogenous gene introduced expressibly into a microorganism that does not express endogenous inositol-1-phosphate synthase, wherein the transformant is characterized by having a gene recombination or mutation to induce the overproduction of functional inositol monophosphatase or activation of inositol monophosphatase.

Embodiments mentioned with regard to the first aspect of the present invention are also applicable to the second aspect of the present invention. These embodiments include:

(14) the transformant according to (13) above, wherein the microorganism that does not express endogenous inositol-1-phosphate synthase is a prokaryote;

(15) the transformant according to (13) or (14) above, wherein the microorganism that does not express endogenous inositol-1-phosphate synthase is a microorganism having an endogenous inositol monophosphatase gene;

(16) the transformant according to any of (13) to (15) above, wherein the microorganism that does not express endogenous inositol-1-phosphate synthase is a bacterium selected from the group consisting of *Escherichia coli*, bacteria belonging to the genus *Bacillus*, bacteria belonging to the genus *Corynebacterium*, and bacteria belonging to the genus *Zymomonas*;

(17) the transformant according to (16) above, wherein the bacterium is *Escherichia coli*.

(18) the transformant according to any of (13) to (17) above, wherein the overproduction of inositol monophosphatase is induced by, in the microorganism, a) introducing an exogenous inositol monophosphatase gene, b) increasing the number of copies of an endogenous inositol monophosphatase gene, c) introducing a mutation into a regulatory region of an endogenous inositol monophosphatase gene, d) substituting the regulatory region of an endogenous inositol monophosphatase gene with a high expression-inducing exogenous regulatory region, or e) deleting the regulatory region of an endogenous inositol monophosphatase gene;

(19) the transformant according to (18) above, wherein the overproduction of inositol monophosphatase is induced by introducing the exogenous inositol monophosphatase gene into the microorganism; and

(20) the transformant according to any of (13) to (17) above, wherein the activation of inositol monophosphatase is induced by, in the above microorganism, f) introducing a mutation into an endogenous inositol monophosphatase gene, g) substituting all or part of the endogenous inositol monophosphatase gene, h) deleting part of the endogenous inositol monophosphatase gene, i) decreasing other proteins that lower inositol monophosphatase activity, or j) decreasing production of compounds that lower the inositol monophosphatase activity.

The third aspect of the present invention is a novel myo-inositol derivative discovered to be produced in the culture of the above transformant. Therefore, the present invention is:

(21) a compound represented by the following structural formula:

[Chemical Formula 2]

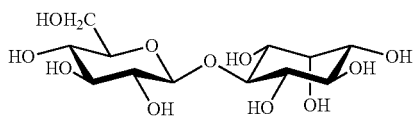

The novel myo-inositol derivative of the present invention was also confirmed to be decomposed easily into glucose and myo-inositol by an enzyme capable of catalyzing a reaction that hydrolyzes β-glycoside bonds (EC 3.2.1.21 and the like). This enzymatic decomposition can be achieved by any of treating the culture obtained in (1) above by this enzyme directly, treating crudely purified product of the culture by this enzyme, or treating the isolated myo-inositol derivative of the present invention by this enzyme. Therefore, the fourth aspect of the present invention is:

(22) a method for producing myo-inositol, wherein the myo-inositol derivative of (21) above is decomposed by an enzyme capable of catalyzing a reaction that hydrolyzes β-glycoside bonds, to produce myo-inositol.

The present invention also intends a composition containing the novel myo-inositol derivative of the present invention. For example, myo-inositol has been widely used as a component of nutritional foods, feeds, drugs, and the like. However, yeasts, bacteria belonging to the genus *Bacillus*, enteric bacteria, and the like that assimilate myo-inositol are present in the environment. Therefore, myo-inositol is preferably protected from the myo-inositol-assimilating bacteria and the like until it is required to manifest its physiological effects when myo-inositol is utilized as a composition for nutritional foods, feeds, drugs, or the like. Whereas, the fifth invention is:

(23) a composition containing the myo-inositol derivative of (21) above.

Advantages of the Invention

The present invention makes it possible to achieve more efficient industrial myo-inositol production through microbial culture techniques. The present invention also provides a novel myo-inositol derivative. The novel myo-inositol derivative of the present invention is easily converted into myo-inositol, but is resistant to microorganisms and the like that assimilate myo-inositol.

BRIEF DESCRIPTION OF THE DRAWINGS

[FIG. 1] shows a coding region of INO1 gene (SEQ ID NO: 1).

[FIG. 2] shows a coding region of the suhB gene (SEQ ID NO: 3).

BEST MODE FOR CARRYING OUT THE INVENTION

Figure 3:
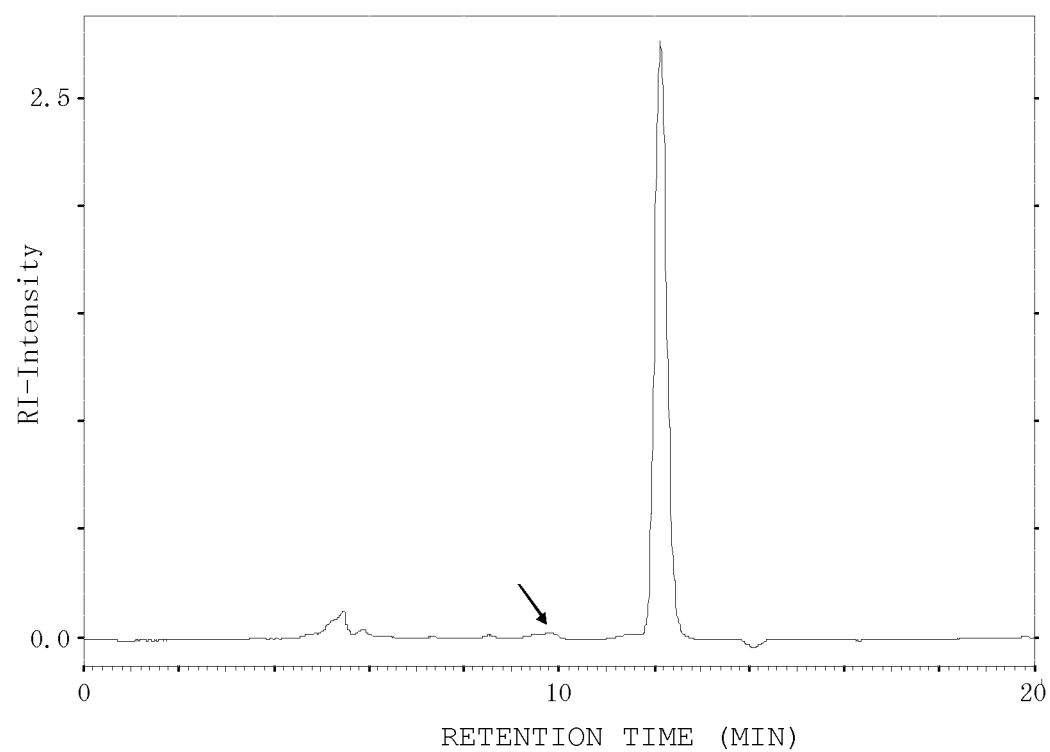
[FIG. 3] shows a production example of the myo-inositol derivative of the present invention. In the figure, the arrow shows a fraction containing the myo-inositol derivative of the present invention. These are the results of analysis by HPLC (mobile phase: water, column temperature: 70° C., flow rate: 1 mL/min, detector: RI) linked to KS-G (guard column), Sugar KS-801 and Sugar KS-802 (all trade names, manufactured by Showa Denko K.K.).
Figure 4:
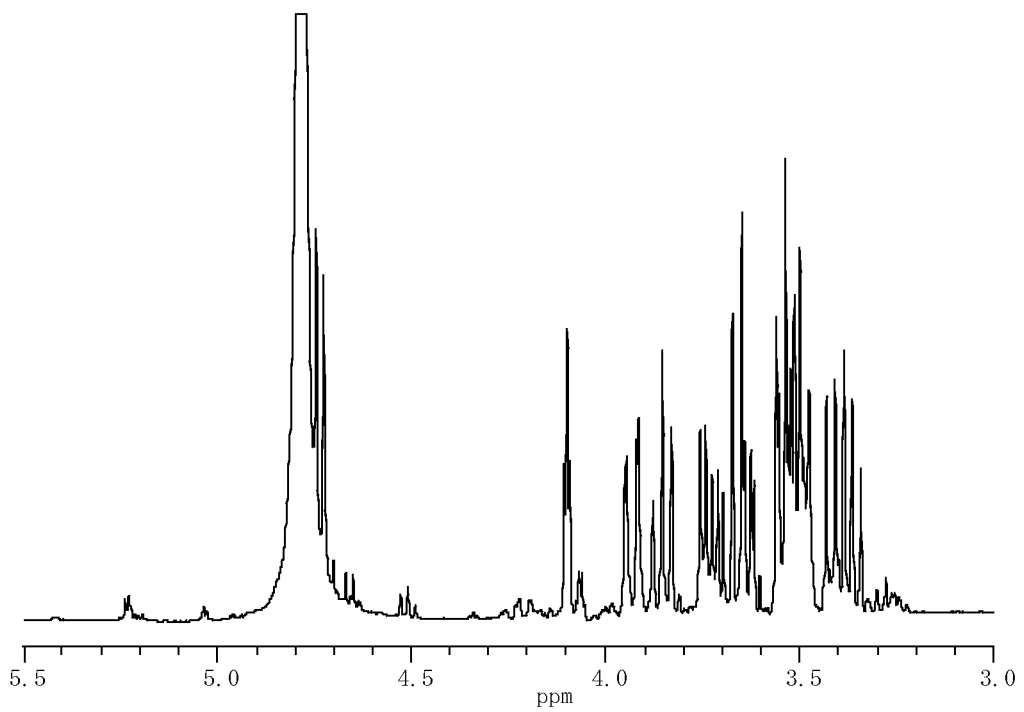
[FIG. 4] is $^1$H-NMR spectrum of the myo-inositol derivative of the present invention.
Figure 5:
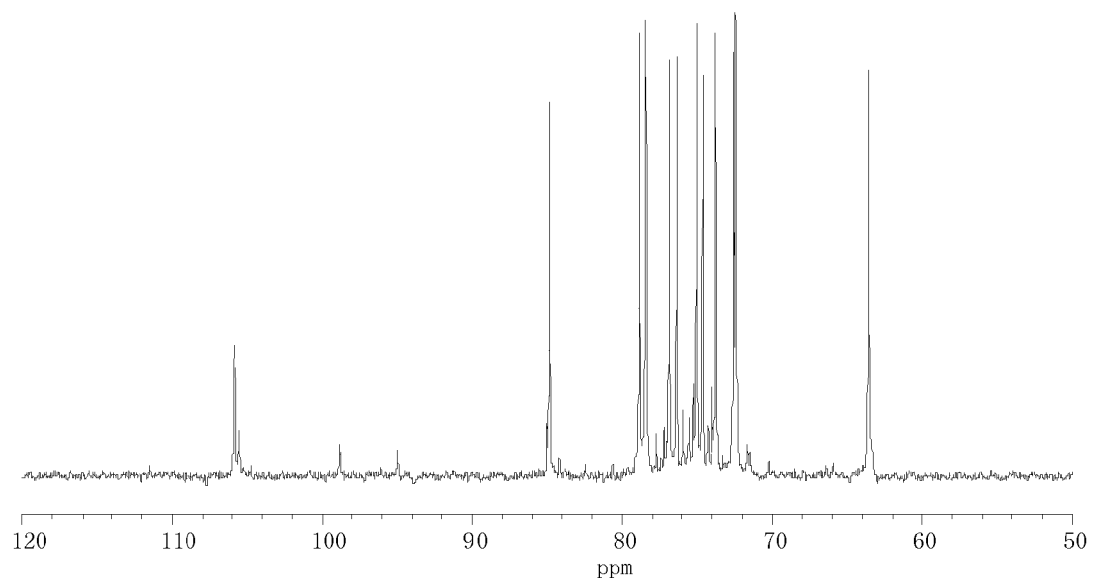
[FIG. 5] is $^{13}$C-NMR spectrum of the myo-inositol derivative of the present invention.

The problem of the present invention is solved by enhancing the inositol monophosphatase activity in a transformant obtained by introducing a myo-inositol biosynthetic pathway into a host microorganism that does not have an endogenous myo-inositol biosynthetic pathway, that is, a transformant obtained by introducing an exogenous gene of endogenous inositol-1-phosphate synthase into a host microorganism that does not express this enzyme. In this specification, the term "exogenous" is used to mean that a gene or nucleic acid sequence based on the present invention is introduced into a host in a case where the host microorganism prior to transformation does not have the gene to be introduced by the present invention, a case where it substantially does not express the enzyme encoded by the gene, and a case where the amino acid sequence of the enzyme is encoded by a different gene, but endogenous enzyme activity comparable to that after transformation is not expressed.

As was mentioned above, the characteristic of the host microorganism of the present invention "does not express endogenous inositol-1-phosphate synthase" makes it possible to newly construct a myo-inositol biosynthetic pathway in the host cell (i.e. without affecting an existing endogenous pathway), and thus this is extremely attractive for the application of synthetic biology techniques. Prokaryotic microorganisms that can be given as examples are bacteria belonging to the genera *Escherichia*, *Pseudomonas*, *Bacillus*, *Geobacillus*, *Methanomonas*, *Methylobacillus*, *Methylophilus*, *Protaminobacter*, *Methylococcus*, *Corynebacterium*, *Brevibacterium*, *Zymomonas*, and *Listeria*. Nonlimiting examples of prokaryotic microorganisms suited to industrial fermentative production include *Escherichia coli*, bacteria belonging to the genus *Bacillus*, bacteria belonging to the genus *Corynebacterium* and bacteria belonging to the genus *Zymomonas*. *Escherichia coli* is a particularly preferred example of the host microorganism of the present invention because of its rapid growth capacity and ease of fermentation control.

Cell lines that can be utilized as host cells of the present invention may be wild types in the ordinary sense or may be auxotrophic mutants or antibiotic-resistant mutants. Cell lines that can be utilized as host cells of the present invention may also be already transformed so as to have various marker genes related to the above mutations. These mutations and genes can provide properties beneficial to the production, maintenance, and control of the transformants of the present invention. Preferably, the use of a strain presenting resistance to chloramphenicol, ampicillin, kanamycin, tetracycline, and the like enables easier production of myo-inositol and the myo-inositol derivative of the present invention.

In the present invention directed toward synthetic biology, an exogenous inositol-1-phosphate synthase gene is introduced into a host microorganism that does not express endogenous inositol-1-phosphate synthase, as described above, to construct a new myo-inositol biosynthetic pathway in the host cell. Inositol-1-phosphate synthase genes are known (for example, GenBank Accession Nos. AB032073, AF056325, AF071103, AF078915, AF120146, AF207640, AF284065, BC111160, L23520, U32511), and any of these can be used for the purposes of the present invention. In particular, IN01 gene derived from yeast (SEQ ID NO: 1) is a well-known example of an inositol-1-phosphate synthase gene and can be used appropriately in the present invention as well. However, inositol-1-phosphate synthase genes that can be utilized in the present invention are not limited to those derived from yeasts and may be derived from other eukaryotic microorganisms and other organisms or may be artificially synthesized, as long as they are capable of expressing substantial inositol-1-phosphate synthase activity within the host microbial cells.

Therefore, inositol-1-phosphate synthase genes that can be utilized for the purposes of the present invention may have any mutations capable of occurring in the natural world and artificially introduced mutations and modifications as long as they are capable of expressing substantial inositol-1-phosphase synthase activity within the host microbial cells. For example, the presence of excess codons (redundancy) is known in various codons that encode specific amino acids. Alternate codons that are finally translated into the same amino acids may therefore also be utilized in the present invention. In other words, since the genetic code degenerates, multiple codons can be used to encode a certain specific amino acid, and the amino acid sequence can therefore be encoded by arbitrary one set of analogous DNA oligonucleotides. While only one member of the set is identical to the genetic sequence of the native enzyme, even mismatched DNA oligonucleotides can hybridize with the native sequence under suitable stringent conditions (for example, hybridization by 3×SSC, 68° C.,; washing by 2×SSC, 0.1% SDS, and 68° C.), and the DNA that encodes the native sequence can be identified and isolated. Such genes can also be utilized in the present invention. In particular, since virtually all organisms are known to use subsets of specific codons (optimal codons) preferentially (Gene, Vol. 105, pp. 61-72, 1991, and the like), "codon optimization" in accordance with the host microorganism can also be useful in the present invention.

Further, those skilled in the art will appreciate that introducing an inositol-1-phosphate synthase gene into the host microbial cells as an "expression cassette" provides a more stable, higher level of inositol-1-phosphate synthase activity in the present invention as well. In this specification, "expression cassette" means a nucleotide containing a nucleic acid sequence that regulates transcription and translation functionally linked to the nucleic acid to be expressed or the gene to be expressed. Typically, an expression cassette of the present invention contains a promoter sequence in 5' upstream from the coding sequence, and a terminator sequence in 3' downstream from the sequence. Sometimes it contains further normal regulatory elements in a functionally linked state, and in such cases the nucleic acid to be expressed or the gene to be expressed is "introduced expressibly" into the host microorganism.

A promoter is defined as a DNA sequence that links RNA polymerase to DNA and initiates RNA synthesis, regardless of whether it is a constitutive promoter or a regulatory promoter. A strong promoter means a promoter that initiates mRNA synthesis at high frequency, and it is also preferably used in the present invention. A lac promoter, trp promoter, TAC or TRC promoter, major operator and promoter regions of λ phage, fd coat protein control region, promoters for a glycolytic enzymes (for example, 3-phosphoglycerate kinase, glyceraldehyde-3-phosphate dehydrogenase), glutamate decarboxylase A, serine hydroxymethyl transferase, and the like can be utilized in accordance with the properties and the like of the host cells. Examples of regulatory elements other than promoter and terminator sequences include selection markers, amplification signals, replication origins, and the like. Suitable regulatory sequences are listed, for example, in "Gene Expression Technology: Methods in Enzymology 185," Academic Press (1990).

The expression cassette explained above is incorporated, for example, into a vector comprised of a plasmid, phage, transposon, IS element, phasmid, cosmid, linear or circular DNA, or the like, and inserted into the host microorganism. Preferred are plasmids and phages. These vectors may be autonomously replicated in the host microorganism or may be replicated through chromosome. Suitable plasmids include, for example, *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III113-B1, λgt11 or pBdCI; *Bacillus* pUB110, pC194 or pBD214; *Corynebacterium* pSA77 or pAJ667; and the like. Plasmids and the like that can also be used in addition to these are listed in "Cloning Vectors," Elsevier, 1985. The expression cassette can be introduced into the vector by conventional methods, including excision by suitable restriction enzymes, cloning, and ligation.

After having constructed the vector having an expression cassette of the present invention as discussed above, for example, coprecipitation, protoplast fusion, electroporation, retrovirus transfection, and other such conventional cloning methods and transfection methods are used as methods that can be used to introduce the vector into the host microorganism. Examples of these are listed in "Current Protocols in Molecular Biology," F. Ausubel et al., Publ. Wiley Interscience, New York, 1997 or Sambrook et al., "Molecular Cloning: Laboratory Manual," $2^{nd}$ edition, Cold Spring Harbor Laboratory, Cold Spring Harbor Laboratory Press, Cold Spring Harbor, N.Y., 1989.

Surprisingly enough, the present inventors discovered that inositol monophosphatase activity plays an important role in the transformants obtained by introducing a myo-inositol biosynthetic pathway into a host microorganism not having an endogenous myo-inositol biosynthetic pathway. As was mentioned above, none of the research conducted up to this point paid any particular attention to inositol monophosphatase activity. However, the enhancement of the inositol monophosphatase activity unexpectedly resulted in great improvement of the ability of such transformants to produce myo-inositol. Such transformants also produced the myo-inositol derivative of the present invention in substantial quantities.

Therefore, one embodiment of the present invention encompasses inducing overproduction of inositol monophosphatase in the above-mentioned host microbial cells transformed by an inositol-1-phosphate synthase-encoding exogenous gene.

The inositol monophosphatase intended in the present invention includes proteins capable of substantially hydrolyzing inositol-1-phosphate by presenting phosphoric monoester hydrolase activity that can act on a wide range of substrates in addition to those presenting high substrate specificity for inositol-1-phosphate. For example, inositol-1-monophosphatase is known as a typical inositol monophosphatase, and this gene (suhB gene) from many organisms has been published in GenBank Accession Nos. ZP_04619988, YP_001451848, and the like. The use of an suhB gene from *E. coli* (SEQ ID NO: 3: AAC75586 (MG1655)) is especially convenient when *E. coli* is used as the host cell.

Those skilled in the art will readily appreciate that the above explanation of mutation, modification, and codon optimization, expression cassette, promoter and other regulator sequences and plasmids and the like, and transformation thereby given with regard to the inositol-1-phosphate synthase gene is also applicable for all of the inositol monophosphatase genes of the present invention. Therefore, it is evident that the overproduction of inositol monophosphatase in the present invention can be achieved by transforming the above-mentioned host microorganism by an expression cassette of an exogenous inositol monophosphatase gene.

Furthermore, many microbial cells are believed to express the inositol monophosphatase activity (that is, to have an endogenous gene that encodes inositol monophosphatase activity) intended in the present invention. Therefore, the overproduction of inositol monophosphatase in the present invention can also be induced by increasing the number of copies of an endogenous inositol monophosphatase gene; introducing a mutation into a regulatory region of the endogenous inositol monophosphatase gene; substituting the regulatory region of the endogenous inositol monophosphatase gene with a high expression-inducing exogenous regulatory region; and deleting the regulatory region of the endogenous inositol monophosphatase gene. Specifically, overexpression of inositol monophosphatase can be achieved by transforming the above-mentioned host microorganism by a construct containing an endogenous inositol monophosphatase gene or an expression cassette having a suitable regulatory region added to the region that encodes the endogenous gene, thereby substantially increasing the number of copies of the inositol monophosphatase gene in the transformant in comparison to that of the original host cell; or mutating, adding, and deleting chromosomes with regard to the original host cell having an endogenous inositol monophosphatase gene by known genetic recombination techniques; or introducing mutations randomly into the chromosomes using a mutagen or the like. The overproduction of inositol monophosphatase can be confirmed by using known SDS-PAGE analytical methods, and the like.

Another embodiment of the present invention to enhance the inositol monophosphatase activity includes inducing activation of inositol monophosphatase in the above-mentioned host microbial cells transformed by an exogenous gene that encodes inositol-1-phosphate synthase. Examples of techniques used for this purpose include 1) introducing a mutation into an endogenous inositol monophosphatase gene, 2) partially or completely substituting the endogenous inositol monophosphatase gene, 3) partially deleting the endogenous inositol monophosphatase gene, 4) decreasing other proteins that lower inositol monophosphatase activity, and/or 5) decreasing production of compounds that lower the inositol monophosphatase activity.

With regard to the above techniques 1)-5) to enhance the inositol monophosphatase activity, inositol monophosphatase having enhanced inositol monophosphatase activity can be obtained by, in particular, subjecting the inositol monophosphatase gene to mutation, addition, or deletion followed by evaluation of the activity of inositol monophosphatase encoded by this gene.

The transformants obtained as described above, for example, transformants transfected by a vector having an exogenous inositol-1-phosphate synthase gene expression cassette and an inositol monophosphatase gene expression cassette, wherein each expression cassette may be placed on a separate vector or the same vector, are cultured and maintained under conditions suited to growth and/or maintenance of the transformants to produce myo-inositol and the myo-inositol derivative of the present invention. Suitable medium compositions, culture conditions, and culture times for transformants derived from various host microbial cells are known to those skilled in the art.

The medium may be natural, semisynthetic, or synthetic medium containing one or more carbon sources, nitrogen sources, inorganic salts, vitamins, and, sometimes, trace components such as trace elements, vitamins, or the like. However, it goes without saying that the medium used must properly satisfy the nutrient requirements of the transformants to be cultured. The medium of the present invention should also contain a carbon source that can ultimately be utilized as a substrate for myo-inositol production, that is, a compound that can be converted into glucose-6-phosphate within the transformant, for bringing the transformant into contact with a carbon source that can be converted into myo-inositol or myo-inositol derivative by the transformant. The carbon source can be D-glucose, sucrose, oligosaccharide, polysaccharide, starch, cellulose, rice bran, or molasses, or a biomass containing D-glucose. Examples of suitable biomasses include decomposed corn solution and decomposed cellulose solution. When the transformants express useful additional traits, for example, when they have antibiotic-resistance markers, the medium may contain the corresponding antibiotics. This reduces the risk of contamination by foreign bacteria during fermentation.

When the host microorganisms cannot assimilate cellulose, polysaccharides, or other such carbon source, the host microorganisms can be adapted to myo-inositol production using these carbon sources by introducing an exogenous gene or other such known genetic engineering techniques. Examples of the exogenous gene include a cellulase gene, amylase gene, and the like.

Culture may be either by batch or continuous. In either case, additional above-mentioned carbon source and the like may be supplied at a suitable point in time during culture. Culture should also be continued while maintaining a suitable temperature, oxygen concentration, pH, and the like. A suitable culture temperature for transformants derived from common microbial host cells is usually within the range of 15-45° C., preferably 25-37° C. When the host microorganism is aerobic, shaking (flask culture and the like), stirring/aeration (jar fermenter culture and the like) are necessary to assure a suitable oxygen concentration during fermentation. These culture conditions are easy to establish for those skilled in the art.

Methods of purifying myo-inositol from the above culture are known to those skilled in the art. In the case of transformants of prokaryotic microbial host cells, myo-inositol is present in the culture supernatant or in the cells, and may be extracted from the cultured cells if necessary. In the case of extracting from cultured cells, for example, the culture is centrifuged to separate the supernatant and cells, and the cells can be broken down with use of surfactant, organic solvent, enzyme, or the like while utilizing a homogenizer. Examples of methods of purifying myo-inositol from the culture supernatant and sometimes from a cell extract include deproteination utilizing protein precipitation by pH adjustment or the like, removal of impurities utilizing adsorption by activated carbon, removal of ionic substances utilizing adsorption by ion-exchange resin or the like, followed by recrystallization of the solid, obtained by drying, from a water-ethanol system, for example. As shall be apparent, some steps may be omitted or additional purification steps such as chromatography may be implemented depending on the target purity of the product.

Furthermore, the novel myo-inositol derivative of the present invention can also be obtained from the above-mentioned culture cultured under appropriate conditions. The typical myo-inositol derivative of the present invention is called 1-4-O-β-D-glucopyranosyl-myo-inositol and has the following structure.

[Chemical Formula 3]

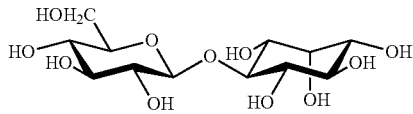

The above myo-inositol derivative is advantageously produced by culturing the transformants of the present invention in medium that is capable of producing a relatively large amount of myo-inositol (for example, about 30-120 g/L). In other words, the transformants of the present invention usually produce more myo-inositol than the myo-inositol derivative of the present invention. However, since the transformants of the present invention can produce not only more myo-inositol but also myo-inositol derivative depending on the amount of glucose added to the medium, as will be illustrated in the examples below, such culture conditions are also suitable for obtaining the myo-inositol derivative of the present invention.

The myo-inositol derivative of the present invention can be crudely purified from the culture in accordance with the methods described above for myo-inositol. For example, the myo-inositol derivative of the present invention can be crudely purified by treating the culture supernatant by activated carbon, then by ion-exchange resin (cation-exchange resin and anion-exchange resin).

However, since the above crudely purified product contains both the myo-inositol derivative of the present invention and myo-inositol, myo-inositol must be separated therefrom in order to isolate the myo-inositol derivative of the present invention. For example, when the above-mentioned crudely purified culture broth contains a large amount of myo-inositol, part of myo-inositol can be removed by precipitation by concentrating the crudely purified solution under reduced pressure, and then filtration and the like. The residual myo-inositol can also be precipitated (crystallized out) by adding ethanol to the filtrate. Therefore, the myo-inositol derivative of the present invention of the desired purity can be obtained by repeating the crystallization by ethanol as appropriate. Alternatively, the myo-inositol derivative of the present invention and myo-inositol can be obtained separately by chromatography, for example, preparative HPLC using Sugar KS-801 and Sugar KS-802 and Shodex Asahipak NH$_2$P-50 4E (all trade names, manufactured by Showa Denko K.K.), alone or in conjunction with crystallization.

The myo-inositol derivative of the present invention was also confirmed to be readily decomposed by β-glucosidase having the ability to hydrolyze β1→4 bonds and to produce the corresponding number of moles of glucose and myo-inositol. To enzymatically decompose the myo-inositol derivative of the present invention by β-glucosidase or the like, a suitable amount of enzyme may be added to a solution of the myo-inositol derivative of the present invention produced by water or buffer (acetate buffer, phosphate buffer, or the like), and the solution may be incubated using conditions and time suitable for the enzymatic reaction. β-glucosidases that can be used advantageously for this purpose are marketed and all can be used, but Cellobiase from molds of the genus *Aspergillus* (Sigma), for example, may be utilized. The amount of enzyme added may be decided as appropriate based on the concentration of the myo-inositol derivative of the present invention in the solution and other such factors by referring to the manufacturer's instructions. The pH during reaction is generally in the range of pH 4.0-9.0, but in essence it should be the optimum pH for the enzyme used. The temperature during reaction should also be within the optimum temperature range of the enzyme used, for example, about 20-50° C. The reaction time should be the time when basically all of the myo-inositol derivative of the present invention has been converted into myo-inositol while quantitatively tracing the decomposition rate of the myo-inositol derivative of the present invention.

Furthermore, as was mentioned above, since the transformants of the present invention produce the myo-inositol derivative of the present invention, together with myo-inositol, at a significantly smaller amount than that of myo-inositol under typical culture conditions, the myo-inositol productivity can be further heightened by, instead, processing the culture of these transformants, which had not been subjected to any treatment, with the above-mentioned enzyme, or by processing with the enzyme after crudely purifying the culture by activated carbon to convert the myo-inositol derivative of the present invention into myo-inositol. Alternatively, myo-inositol may be obtained by processing with β-glucosidase after having isolated the myo-inositol derivative of the present invention. Those skilled in the art will appreciate the benefit of maintaining myo-inositol in the form of the myo-inositol derivative of the present invention until use (or until the time to express physiological action) since the myo-inositol derivative of the present invention is resistant to ubiquitous organisms capable of assimilating myo-inositol (yeasts, *Bacillus subtilis*, enteric bacteria).

Therefore, use of the myo-inositol derivative of the present invention as an active ingredient or functional component of drugs, foods, cosmetics, and the like is also one of potential applications thereof. In other words, since myo-inositol is an essential substance for many higher animals, as was mentioned above, it is widely utilized as a component of nutritional foods, feeds, drugs, and the like. For example, myo-inositol is known to play an important role in the metabolism of fats and cholesterols and is said to be effective especially in the prevention and treatment of hypercholesterolemia and the like. Since the myo-inositol derivative of the present invention is enzymatically decomposed and produces myo-inositol easily, the addition of the myo-inositol derivative itself of the present invention to drugs and the like, with the expectation that myo-inositol derivative of the present invention would be enzymatically decomposed in the body to produce myo-inositol, is a very interesting practical embodiment of the present invention.

For example, pharmaceutical compositions containing the myo-inositol derivative of the present invention as an active ingredient can be in an oral dosage form such as a tablet, powder, granule, capsule, sugar-coated tablet, solution, and syrup agent, or in a parenteral dosage form such as an injection, infusion, suppository, percutaneous agent and absorbable agent. Various carriers are used depending on these formulations. Examples of carriers for oral agents include excipients such as lactose, sucrose, glucose, mannitol, erythritol, xylitol, maltitol, sorbitol, various types of starch, crystalline cellulose, and powdered cellulose, binders such as dextrin, gum Arabic, sodium alginate, povidone, polyvinyl alcohol, methylcellulose, hydroxypropylcellulose, hydroxypropylcellulose with low degree of substitution, and carmellose sodium, lubricants such as stearic acid, calcium stearate, magnesium stearate, and talc, flow promoters such as hydrated silicon dioxide, light silicic anhydride, and titanium oxide, and colorants.

The dose of the pharmaceutical composition is not particularly limited. For example, 0.01-2000 mg of active ingredient per day can be administered to an adult from once to several times by dividing the amount. An administration frequency may be varied from monthly to daily, and it is preferably from once a week to three times a week or five times a week or daily. The daily dose, duration of administration, and administration frequency may also be increased or decreased as appropriate in accordance with the patient's age, weight, physical health, condition to be treated, its severity, and other such factors.

Those skilled in the art who contact the above explanation can implement the present invention adequately. Examples are given below for the sake of further explanation. Therefore, the present invention is not limited to these examples. Furthermore, the nucleotide sequences in this specification are listed in the direction from 5' to 3' unless stated otherwise.

EXAMPLES

Example 1

Construction of a Plasmid 1-a) Inositol Monophosphatase Expression Cassette E. coli W3110 (NBRC 12713) was shake-cultured at 37° C. in LB medium (2 mL). After completion of culture, the cells were collected from the culture broth, and the genomic DNA was extracted using Nucleo Spin Tissue (product name, manufactured by Macherey-Nagel). Using the extracted genomic DNA as a template, PCR amplification was carried out with use of the primers below to clone the coding region of the suhB gene (SEQ ID NO: 3) (PrimeSTAR Max DNA Polymerase (product name, manufactured by Takara Bio), reaction conditions: 98° C. 10 sec, 55° C. 5 sec, 72° C. 20 sec, 28 cycles).

[Chemical Formula 4]
```
                                     (SEQ ID NO: 5)
Forward: a t g c a t c c g a t g c t g a a c (SEQ ID NO: 6)
Reverse: t t a a c g c t t c a g a g c g t c g
```

The suhB coding region obtained was inserted transcribably in the downstream of a promoter of the following sequence.

[Chemical Formula 5]
Promoter:
```
                                     (SEQ ID NO: 7)
g t c g t t t t t c t g c t t a g g a t t t t g t t a t t t a a a t t a a g c c t g t a a t g c c t t g c t t c c a t t g c g g a t a a a t c c t a c t t t t t t a t t g c c t t c a a a t a a a t t a a g g a g t t c
```

Specifically, a terminator sequence and the above promoter sequence were inserted in the multicloning site of plasmid pNFP-A51 (deposited as FERM ABP-11515 on Oct. 25, 2011 at the International Patent Organism Depository, National Institute of Advanced Industrial Science and Technology).

The suhB coding region cloned as described above was ligated to the downstream of the inserted promoter sequence to construct pNFP-A54. The pNFP-A54 constructed was transfected into E. coli AKC-016 (deposited as FERM ABP-11512 on Apr. 20, 2011 at the International Patent Organism Depository, National Institute of Advanced Industrial Science and Technology) by calcium chloride method (refer to Genetic Engineering Laboratory Notebook, by Takaaki Tamura, Yodosha). High expression of inositol monophosphatase was confirmed in the soluble fraction of this E. coli by SDS-PAGE.

1-b) Inositol-1-Phosphate Synthase Expression Cassette

The cells were collected from the culture broth of isolated distillery yeast, and the genomic DNA was extracted using Nucleo Spin Tissue (product name, manufactured by Macherey-Nagel). Using the extracted genomic DNA as a template, PCR amplification was carried out with use of the following primers to clone the coding region of the INO1 gene (SEQ ID NO: 1) (PrimeSTAR Max DNA Polymerase (product name, manufactured by Takara Bio), reaction conditions: 98° C. 10 sec, 55° C. 5 sec, 72° C. 20 sec, 28 cycles).

[Chemical Formula 6]
Forward:
```
                                     (SEQ ID NO: 8)
a t g a c a g a a g a t a a t a t t g c t c
```

Reverse:
```
                                     (SEQ ID NO: 9)
t t a c a a c a a t c t c t c t t c g
```

The ino1 coding region obtained was inserted transcribably in the downstream of a promoter of the following sequence.

[Chemical Formula 7]
Promoter:
```
                                     (SEQ ID NO: 10)
c t c a a g c c c a a a g g a a g a g t g a g g c g a g t c a g t c g c g t a a t g c t t a g g c a c a g g a t t g a t t t g t c g c a a t g a t t g a c a c g a t t c c g c t t g a c g c t g c g t a a g g t t t t t g t a a t t t t a c a g g c a a c c t t t t a t t c a c t a a c a a a t a g c t g g t g g a a
```

Specifically, a terminator sequence and the above promoter sequence were inserted in the multicloning site of the above plasmid pNFP-A51.

The ino1 coding region cloned as described above was ligated to the downstream of the inserted promoter sequence to construct pNFP-D78. The pNFP-D78 constructed was transfected into E. coli AKC-016 (deposited as FERM ABP-11512 on Apr. 20, 2011 at the International Patent Organism Depository, National Institute of Advanced Industrial Science and Technology) by the calcium chloride method (refer to Genetic Engineering Laboratory Notebook, by Takaaki Tamura, Yodosha). High expression of inositol-1-phosphate synthase was confirmed in the soluble fraction of this E. coli by SDS-PAGE.

1-c) Construction of a Plasmid for Transformation p-NFP-D78 was subjected to blunting and 5' end dephosphorylation by digestion with use of Sal I. The suhB expression cassette in pNFP-A54 was cloned, and ligated into pNFP-D78. pNFP-G22 was obtained, in which an INO1 expression cassette in pNFP-D78 and an suhB expression cassette were ligated in the forward direction.

Example 2

Myo-Inositol Production 2-a) Myo-Inositol Production by Transformants Transfected with an Expression Cassette-Containing Plasmid The plasmid pNFP-G22 constructed according to the procedure of Example 1 was transfected into *E. coli* AKC-016 (deposited as FERM ABP-11512 on Apr. 20, 2011 at the International Patent Organism Depository, National Institute of Advanced Industry Science and Technology) by the calcium chloride method (refer to Genetic Engineering Laboratory Notebook, by Takaaki Tamura, Yodosha). This transformant was named as AKC-016-G22.

On the other hand, a control transformant, which had been obtained by transfection with plasmid pNFP-D78 containing only an INO1 expression cassette, and it was named as AKC-016-D78. Each of the transformants obtained was cultured for one day at 37° C. on an LB plate containing ampicillin (100 mg/L) to form colonies. 2 mL of LB medium containing ampicillin (100 mg/L) was loaded in a 15 mL test tube and inoculated by a platinum loop with colonies from the above plate. Culture was carried out at 37° C. for 3-5 hours at 180 rpm until OD (600 nm) reached approximately 0.5, and the obtained culture was used as preculture broth for the main culture.

10 g/L, 15 g/L, or 30 g/L of glucose and 100 mL of synthetic medium (table below) containing 100 mg/L of ampicillin or LB medium were loaded in a 250 mL jar culture apparatus (instrument name Bio Jr. 8, manufactured by Biott); 2 mL of the preculture broth was added, and conducted main culture (myo-inositol production test). The culture conditions were as follows: Culture temperature 30° C.; culture pH 6.7; alkali added 10% (W/V) ammonia water; stirring at 1200 rpm; ventilation 0.1 vvm.

TABLE 1

| Synthetic medium composition | |
| --- | --- |
| $KH_2PO_4$ | 13.3 g |
| $(NH_4)_2HPO_4$ | 4 g |
| $MgSO_4 \cdot 7H_2O$ | 1.2 g |
| $EDTA \cdot 2Na$ | 8.4 mg |
| $CoCl_2 \cdot 6H_2O$ | 2.5 mg |
| $MnCl_2 \cdot 4H_2O$ | 15 mg |
| $CuCl_2 \cdot 2H_2O$ | 1.5 mg |
| $H_3BO_3$ | 3 mg |
| $Na_2MoO_4 \cdot 2H_2O$ | 2.5 mg |
| $Zn(CH_3COO)_2 \cdot 2H_2O$ | 13 mg |
| $FeCl_3 \cdot 6H_2O$ | 100 mg |
| total | 1 L |

Adjusted to pH 6.7 using 8N KOH.

The above culture broth was centrifuged at 4° C. for 10 min at 10,000×g, and the supernatant was collected. The myo-inositol concentration in the culture supernatant was measured. Specifically, the myo-inositol concentration in the culture supernatant was assayed by HPLC (detector: RI, column temperature: 70° C., flow rate: 1 mL/min,) linked to KS-G (guard column) and Sugar KS-801 and Sugar KS-802 (all trade names, manufactured by Showa Denko K.K.). The results comparing the transformant of the present invention (AKC-016-G22) and the control strain (AKC-016-D78) are shown in Table 2 (synthetic medium) and Table 3 (LB medium).

TABLE 2

| Myo-inositol concentration (g/L) produced in culture supernatant of synthetic medium | | |
| --- | --- | --- |
| Culture time (h) | Strain with inositol monophosphatase gene introduced (strain of the invention: AKC-16-G22) | Strain without inositol monophosphatase gene (control strain: AKC-016-D78) |
| Glucose concentration 10 g/L 18 | 0.57 | 0.17 |
| Glucose concentration 15 g/L 21 | 0.79 | 0.36 |
| Glucose concentration 30 g/L 23 | 1.71 | 0.46 |

TABLE 3

| Myo-inositol concentration (g/L) produced in culture supernatant of LB medium | | |
| --- | --- | --- |
| Culture time (h) | Strain with inositol monophosphatase gene introduced (strain of the invention: AKC-16-G22) | Strain without inositol monophosphatase gene (control strain: AKC-016-D78) |
| Glucose concentration 10 g/L 18 | 1.12 | 0.75 |
| Glucose concentration 15 g/L 21 | 1.63 | 0.96 |
| Glucose concentration 30 g/L 23 | 2.31 | 1.39 |

2-b) Myo-Inositol Production by a Transformant Having a Expression Cassette on Chromosome In this example, a transformant having both an INO1 expression cassette and suhB expression cassette on chromosome was also produced (*E. coli* AKC-018, deposited as FERM ABP-11514 on Oct. 25, 2011 at the International Patent Organism Depository, National Institute of Advanced Industrial Science and Technology).

On the other hand, a control transformant was obtained by incorporating only an INO1 expression cassette on chromosome (*E. coli* AKC-017, deposited as FERM ABP-11513 on Oct. 25, 2011 at the International Patent Organism Depository, National Institute of Advanced Industrial Science and Technology).

Each of the transformants obtained was precultured in ampicillin-free LB medium, and then subjected to culture to produce myo-inositol under the same culture conditions as in Example 2-a) using the same synthetic medium and LB medium as in Example 2-a) except that it did not contain ampicillin and the amount of glucose added was 10 g/L or 30 g/L. Then, the myo-inositol concentration in the culture supernatant was assayed by a method similar to that of Example 2-a). The results obtained by comparing the transformant of the present invention (AKC-018) and the control strain (AKC-017) are shown in Table 4 (synthetic medium) and Table 5 (LB medium).

TABLE 4

Myo-inositol concentration (g/L) produced in culture supernatant of synthetic medium

|  | Culture time (h) | Strain with inositol monophosphatase gene introduced (strain of the invention: AKC-018) | Strain without inositol monophosphatase gene (control strain: AKC-017) |
| --- | --- | --- | --- |
| Glucose concentration 10 g/L | 18 | 0.22 | 0.06 |
| Glucose concentration 30 g/L | 18 | 0.90 | 0.25 |

TABLE 5

Myo-inositol concentration (g/L) produced in culture supernatant of LB medium

|  | Culture time (h) | Strain with inositol monophosphatase gene introduced (strain of the invention: AKC-018) | Strain without inositol monophosphatase gene (control strain: AKC-017) |
| --- | --- | --- | --- |
| Glucose concentration 10 g/L | 18 | 0.70 | 0.18 |
| Glucose concentration 30 g/L | 23.5 | 1.84 | 0.35 |

The results of the above Examples 2-a) and 2-b) showed that, although the presence of endogenous inositol monophosphatase activity was confirmed in the *E. coli* host (control strain), this activity was not adequate in conventional myo-inositol production by synthetic biology techniques. Surprisingly enough, enhancing the inositol monophosphatase activity in this host improved the myo-inositol productivity about 1.5-5 times in comparison to the control. Also surprisingly, the amount of myo-inositol produced increased in direct proportion to the amount of glucose supplied in microorganisms having enhanced inositol monophosphatase activity. This, contrary to common general technical knowledge, demonstrates the important role of inositol monophosphatase activity in myo-inositol production by synthetic biology techniques.

Example 3

Novel Myo-Inositol Derivative 3-a) Production of a Novel Myo-Inositol Derivative This example shows the production of a novel myo-inositol derivative by AKC-016-G22, which is the transformant of the present invention obtained in Example 2-a).

100 mL of LB medium containing ampicillin (100 mg/L) was loaded in a 500 mL test tube and inoculated by a platinum loop with colonies from a plate where AKC-016-G22 had been cultured. Culture was carried out at 37° C. for 3-5 hours at 180 rpm until OD (600 nm) reached approximately 0.5. This was used as preculture broth for the main culture.

15 g/L of glucose and 3 L of the following synthetic medium (Table 6) containing 100 mg/L of ampicillin were loaded in a 10 L jar culture apparatus (manufactured by Marubishi Bio-engineering); 60 mL of preculture broth was added, and the main culture was conducted. The culture conditions were as follows: Culture temperature 32° C.; culture pH 6.0 [lower limit]; alkali added 28% (w/v) ammonia water; stirring at 850 rpm; ventilation 1 vvm. The glucose feed solution (Table 7) that served as a raw material was added as appropriate so that the glucose concentration in the culture broth would be 0-5 g/L.

TABLE 6

| Synthetic medium composition | |
| --- | --- |
| $KH_2PO_4$ | 13.3 g |
| $(NH_4)_2HPO_4$ | 4 g |
| $MgSO_4 \cdot 7H_2O$ | 1.2 g |
| $EDTA \cdot 2Na$ | 8.4 mg |
| $CoCl_2 \cdot 6H_2O$ | 2.5 mg |
| $MnCl_2 \cdot 4H_2O$ | 15 mg |
| $CuCl_2 \cdot 2H_2O$ | 1.5 mg |
| $H_3BO_3$ | 3 mg |
| $Na_2MoO_4 \cdot 2H_2O$ | 2.5 mg |
| $Zn(CH_3COO)_2 \cdot 2H_2O$ | 13 mg |
| $FeCl_3 \cdot 6H_2O$ | 100 mg |
| total | 1 L |

Adjusted to pH 6.7 using 8N KOH.

TABLE 7

| Glucose feed solution | |
| --- | --- |
| Glucose | 700 g |
| $MgSO_4 \cdot 7H_2O$ | 20 g |
| $EDTA \cdot 2Na$ | 13 mg |
| $CoCl_2 \cdot 6H_2O$ | 5 mg |
| $MnCl_2 \cdot 4H_2O$ | 29 mg |
| $CuCl_2 \cdot 2H_2O$ | 4 mg |
| $H_3BO_3$ | 5 mg |
| $Na_2MoO_4 \cdot 2H_2O$ | 4 mg |
| $Zn(CH_3COO)_2 \cdot 2H_2O$ | 21 mg |
| $FeCl_3 \cdot 6H_2O$ | 41 mg |
| total | 1 L |

After culturing for 69.5 hours, part of the above culture broth was centrifuged at 4° C. for 10 min at 10,000×g, and the supernatant was collected. The supernatant was analyzed by HPLC (mobile phase: water, column temperature: 70° C., flow rate: 1 mL/min, detector: R1) linked to KS-G (guard column) and Sugar KS-801 and Sugar KS-802 (all trade names, manufactured by Showa Denko K.K.). The myo-inositol concentration was 102 g/L.

On the other hand, the novel myo-inositol derivative of the present invention (1-4-O-β-D-glucopyranosyl-myo-inositol) had a retention time of 17.4 minutes in analysis by HPLC (mobile phase: water/acetonitrile=25/75, column temperature: 40° C., flow rate: 0.8 mL/min, detector: R1) using Shodex Asahipak $NH_2P$-50 4E (trade name, manufactured by Showa Denko K.K.) (the retention time of myo-inositol in this analysis was 13 minutes), and was contained at a concentration of 0.3 g/L in the above supernatant.

3-b) Isolation of the Novel Myo-Inositol Derivative

After centrifuging 1000 mL of culture broth obtained as described above for 20 minutes at 8,800 rpm using a large centrifuge, it was centrifuged for five minutes at 13,000 rpm using a small centrifuge. The solids were filtered out from the obtained supernatant by vacuum filtration using a 0.45 pm filter (Millipore, omnipore membrane, model no. JHWP09025). After filtration, 5 g of activated carbon Shirasagi A (trade name, manufactured by Japan Enviro-Chemicals) was added to 1000 mL of filtrate and stirred for 30 minutes by a stirrer. The activated carbon was filtered out from this solution by vacuum filtration using a 0.45 μm filter. After the activated carbon treatment, 500 mL of cation-exchange resin (Amberlite IR120B $H^+$ type manufactured by Organo) was added to the filtrate and stirred for 30 minutes by a stirrer. The cation-exchange resin was filtered out from this solution by vacuum filtration using a 0.45 μm filter. After cation-exchange treatment, 500 mL of anion-exchange resin (Amberlite IRA96SB $OH^-$ type manufactured by Organo) was added to the filtrate and stirred for 30 minutes by a stirrer. The anion-exchange resin was filtered out from this solution by vacuum filtration using a 0.45 μm filter.

After anion-exchange treatment, water was distilled off from 1000 mL of filtrate by an evaporator at 70° C., 100 mbar, to concentrate four-fold until the volume becomes 250 mL. After cooling naturally to room temperature, it was stored at 4° C. After precipitating the myo-inositol, the myo-inositol was filtered out by vacuum filtration. 189 mL of the filtrate contained 5.83% myo-inositol and 0.131% myo-inositol derivative of the present invention (both W/V). Then, 189 mL of ethanol was added to this solution at room temperature. After further precipitating the myo-inositol, the myo-inositol was filtered out by vacuum filtration. 373 mL of the filtrate contained 1.41% myo-inositol and 0.067% myo-inositol derivative of the present invention. The ethanol was distilled off from the filtrate using an evaporator (70° C., 100 mbar), and 62 mL of aqueous solution of 8.46% myo-inositol and 0.401% myo-inositol derivative of the present invention was obtained. 186 mL of ethanol was added at room temperature. After precipitating the myo-inositol, the myo-inositol was filtered out by vacuum filtration. 244 mL of filtrate contained 0.33% myo-inositol and 0.100% myo-inositol derivative of the present invention. The ethanol and water were distilled off from the filtrate using an evaporator (70° C., 100 mbar), and 24 mL of solution of 3.30% myo-inositol and 0.998% myo-inositol derivative of the present invention was obtained.

Presence of substances (structure unidentified), which are multiple impurities that were difficult to separate from myo-inositol and myo-inositol derivative of the present invention, was confirmed other than those two in the above solution and thus various purification methods were studied. As a result, enzyme treatment was effective. Specifically, 300 μL of 150 mM Bis-Tris (pH 7.0) buffer and 200 μL of 100 UN/mL α-glucosidase (manufactured by Sigma-Aldrich, from *Bacillus stearothermophilus*) were added to 500 μL of the above mixed solution of myo-inositol and the myo-inositol derivative of the present invention and reacted for 22 hours while stirring at 1200 rpm at a reaction temperature of 40° C. using an incubator (AS ONE SI-300C). After the reaction, decomposition of one of the above impurities was confirmed by HPLC analysis. Thereafter, the reaction solution was heated for five minutes by a 99° C. dry block bath (manufactured by Sibata, BI-1200), and the enzyme was inactivated. After centrifuging the reacted solution, the supernatant was filtered using a 0.45 μm filter. After freeze drying the filtrate, water was added until the volume of aqueous solution becomes 5 mL. 300 μL of 150 mM Bis-Tris (pH 7.0) buffer and 200 μL of 100 UN/mL β-glucosidase (manufactured by Oriental Yeast Co., Ltd., from almonds) were added to 500 μL of this solution and reacted for a short time, i.e. 0.5 hour, while stirring at 1200 rpm at a reaction temperature of 40° C. using an incubator. After the reaction, decomposition of another impurity was confirmed by HPLC analysis. Thereafter, the reaction solution was heated for five minutes by 99° C. dry block bath, and the enzyme was inactivated. After centrifugation, the supernatant was filtered using a 0.45 μm filter. After freeze drying the filtrate, water was added to prepare an aqueous solution (2.5 mL) containing approximately 0.99% of the myo-inositol derivative of the present invention.

Using the aqueous solution after purifying through enzymatic decomposition as described above, HPLC fractionation was carried out 200 times using a one-time charge of 10 μL. The HPLC conditions during fractionation were as follows.

Column: Shodex Asahipak $NH_2P$-50 4E,

Mobile phase: Water/acetonitrile=25/75

Flow rate: 0.8 mL/min

Temperature: 40° C.

Detector: RI

Autosampler: Shimadzu SIL-20A, total-volume injection type

From the samples after HPLC fractionation acetonitrile was distilled off by an evaporator (70° C., 100 mbar), and water was also removed by freeze drying to obtain a dried solid of the myo-inositol derivative of the present invention (yield: 19 mg).

3-c) Determination of the Structure of the Novel Myo-Inositol Derivative

The structure of the compound separated in Example 3-b) was determined by NMR analysis as follows.

Instrument: Avance 600 (manufactured by Bruker Biospin)

Probe: Cryoprobe ($^{13}C$ high sensitivity)

Measurement temperature: 18° C. (all set at 291K (18° C.) to prevent deterioration of the sample and to shift the water signal during $^1H$-NMR.)

Solvent: $D_2O$ (manufactured by Aldrich)

Internal standard: TSP $^1H$ observed frequency: 600.13 MHz $^{13}C$ observed frequency: 150.92 MHz The results of measurement and assignment of peaks were as follows. Furthermore, the peak number "GH-1" in the table shows the position 1 hydrogen of the glucose residue. "IH-1" shows the position 1 hydrogen of the myo-inositol residue. The others are also the same.

[Chemical Formula 8]

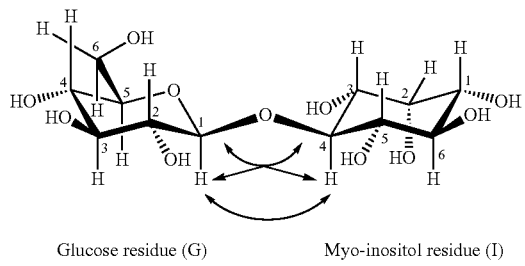

Glucose residue (G)    Myo-inositol residue (I)

TABLE 8

$^1$H-NMR

| Peak no. | δH (ppm) | Peak splitting pattern | J (Hz) |
|---|---|---|---|
| GH-1 | 4.75 | d | 7.9 |
| GH-2 | 3.36 | dd | 7.9, 9.5 |
| GH-3 | 3.53 | dd | 9.5, 9.5 |
| GH-4 | 3.40 | dd | 9.5, 9.5 |
| GH-5 | 3.50 (hypothesized) | ddd (hypothesized: complex splitting) | 9.5, 2.3, 6.4 |
| GH-6 | 3.93 | dd | 2.3, 12.5 |
| GH-6' | 3.73 | dd | 12.5, 6.4 |
| IH-1 | 3.55 | dd | 3.0, 9.8 |
| IH-2 | 4.09 | dd | 3.0, 3.0 |
| IH-3 | 3.63 | dd | 3.0, 9.8 |
| IH-4 | 3.85 | dd | 9.8, 9.8 |
| IH-5 | 3.50 | dd | 9.8, 9.8 |
| IH-6 | 3.67 | dd | 9.8, 9.8 |

TABLE 9

$^{13}$C-NMR

| Peak no. | δ C (ppm) |
|---|---|
| GC-1 | 105.9 |
| GC-2 | 76.4 |
| GC-3 | 78.4 |
| GC-4 | 72.4 |
| GC-5 | 78.9 |
| GC-6 | 63.6 |
| IC-1 | 73.8 |
| IC-2 | 74.7 |
| IC-3 | 72.6 |
| IC-4 | 84.7 |
| IC-5 | 76.9 |
| IC-6 | 75.1 |

The assignment of peaks was also confirmed by COSY, CH-COSY, HMBC, and J-resolved two-dimensional NMR.

3-d) Enzymatic Decomposition of the Novel Myo-Inositol Derivative

The compound separated in Example 3-b) was decomposed by Cellobiase (Sigma), which is a β-glucosidase derived from mold of the genus *Aspergillus*. Specifically, the compound was dissolved in 400 μL of 150 mM Bis-Tris buffer (pH=7.0) at a concentration of 6 mg/mL. 100 μL of 25 U/mL Cellobiase was added to the solution and reacted by incubating (1200 rpm, Bioshaker M·BRO22, Taitec) up to 22 hours at 40° C. The reaction solution was sampled after 0, 3, and 22 hours of the reaction, and the reaction status was confirmed by HPLC (column: Shodex Asahipak NH$_2$P-50 4E (trade name), mobile phase: water/acetonitrile=25/75, flow rate: 0.8 mL/min, column temperature: 40° C., detector: RI).

Figure 6:
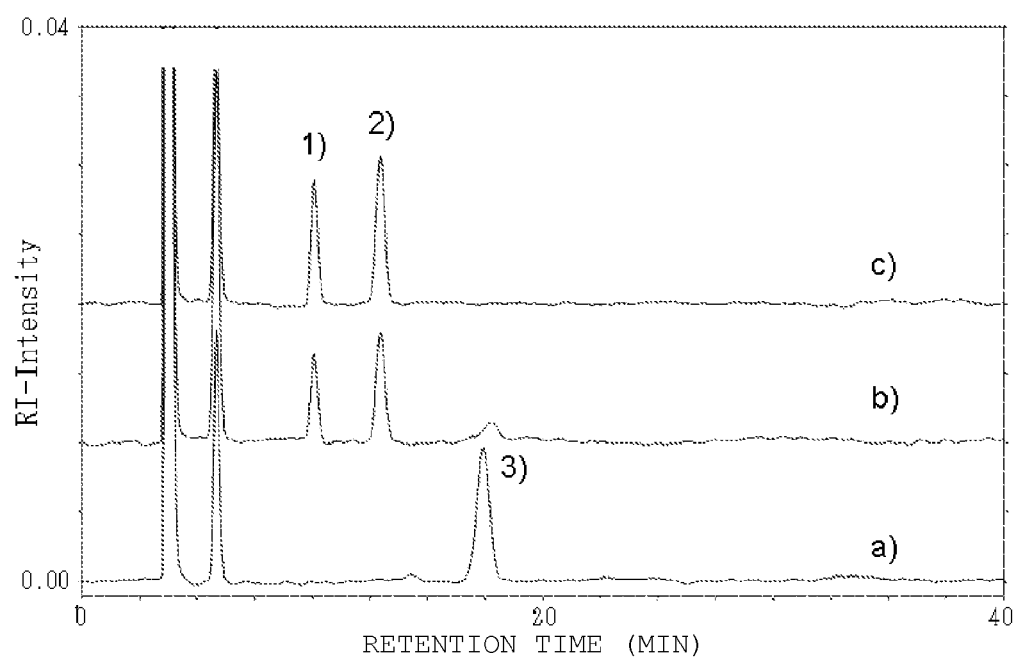
[FIG. 6] is an example of decomposition of the myo-inositol derivative of the present invention by β-glucosidase. These are the results of analysis by HPLC (mobile phase: water/acetonitrile=25/75, column temperature: 40° C., flow rate: 0.8 mL/min, detector: RI) using Shodex Asahipak NH$_2$P-50 4E (trade name, manufactured by Showa Denko K.K.).

As shown by the results in FIG. 6, the myo-inositol derivative of the present invention was mostly decomposed after 3 hours from the start of the reaction, and corresponding amounts of glucose and scyllo-inositol were produced. The myo-inositol derivative of the present invention was completely decomposed after 22 hours from the start of the reaction. The results demonstrated that the myo-inositol derivative of the present invention is easily decomposed by β-glucosidase. This enzyme experiment also confirmed the correctness of the structure determined for the myo-inositol derivative of the present invention.

INDUSTRIAL APPLICABILITY

The present invention can be utilized in the industrial fermentative production of myo-inositol and derivatives thereof.

---

The invention claimed is:

1. A method of producing a myo-inositol or a myo-inositol derivative, comprising:

1) preparing a transformant of a prokaryote microorganism, the transformant containing at least an inositol-1-phosphate synthase-encoding exogenous gene introduced expressibly into the transformant, wherein said prokaryote microorganism (i) does not express endogenous inositol-1-phosphate synthase, (ii) has an endogenous inositol monophosphatase gene, and (iii) is introduced with an exogenous inositol monophosphatase gene to induce overproduction of functional inositol monophosphatase within the transformant; and 2) bringing the transformant into contact with a carbon source that is converted into the myo-inositol derivative by the transformant under conditions suited to growth and/or maintenance of the transformant, wherein said myo-inositol derivative is a compound of Chemical Formula 1:

(Chemical Formula 1)

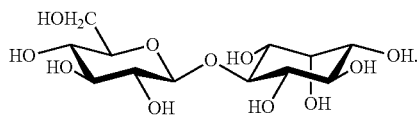

2. The method of claim 1, wherein the prokaryote microorganism that does not express endogenous inositol-1-phosphate synthase is a bacterium selected from the group consisting of *Escherichia coli*, bacteria belonging to the genus *Bacillus*, bacteria belonging to the genus *Corynebacterium*, and bacteria belonging to the genus *Zymomonas*.

3. The method according to claim 2, wherein the bacterium is *Escherichia coli*.

4. The method of claim 1, wherein the carbon source contains a compound that is converted into glucose-6-phosphate within the transformant.

5. The method according to claim 4, wherein the carbon source is selected from the group consisting of D-glucose, sucrose, oligosaccharide, polysaccharide, starch, cellulose, rice bran, molasses, and biomass containing D-glucose.

6. The method of claim 1, further comprising separating the myo-inositol derivative amassed in a culture of the transformant grown and/or maintained in contact with the carbon source.

7. A method of producing myo-inositol comprising providing β glucosidase to catalyze a reaction that hydrolyzes β glycoside bond of a compound of Chemical Formula 2 to produce myo-inositol (Chemical Formula 2)

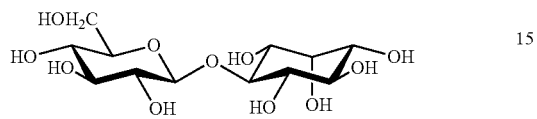

* * * * *

SEQUENCE LISTING

```
<160> NUMBER OF SEQ ID NOS: 10

<210> SEQ ID NO 1
<211> LENGTH: 1602
<212> TYPE: DNA
<213> ORGANISM: Saccharomyces cerevisiae
<220> FEATURE:
<221> NAME/KEY: CDS
<222> LOCATION: (1)..(1602)

<400> SEQUENCE: 1 atg aca gaa gat aat att gct cca atc acc tcc gtt aaa gta gtt acc      48
Met Thr Glu Asp Asn Ile Ala Pro Ile Thr Ser Val Lys Val Val Thr
1               5                   10                  15 gac aag tgc acg tac aag gac aac gag ctg ctc acc aag tac agc tac      96
Asp Lys Cys Thr Tyr Lys Asp Asn Glu Leu Leu Thr Lys Tyr Ser Tyr
                20                  25                  30 gaa aat gct gta gtt acg aag aca gct agt ggc cgc ttc gat gtc acg     144
Glu Asn Ala Val Val Thr Lys Thr Ala Ser Gly Arg Phe Asp Val Thr
            35                  40                  45 ccc act gtt caa gac tac gtg ttc aaa ctt gac tta aaa aag ccg gaa     192
Pro Thr Val Gln Asp Tyr Val Phe Lys Leu Asp Leu Lys Lys Pro Glu
        50                  55                  60 aaa cta gga att atg ctc att ggg tta ggt ggc aac aat ggc tcc acc     240
Lys Leu Gly Ile Met Leu Ile Gly Leu Gly Gly Asn Asn Gly Ser Thr
65                  70                  75                  80 tta gtg gcc tcg gta ttg gcg aat aag cac aat gtg gag ttt caa act     288
```

```
Leu Val Ala Ser Val Leu Ala Asn Lys His Asn Val Glu Phe Gln Thr
                 85              90              95 aag gaa ggc gtt aag caa cca aac tac ttc ggc tcc atg act caa tgt      336
Lys Glu Gly Val Lys Gln Pro Asn Tyr Phe Gly Ser Met Thr Gln Cys
            100             105             110 tct acc ttg aaa ctg ggt gtc gat gcg gag ggg aat gac gtt tat gct      384
Ser Thr Leu Lys Leu Gly Val Asp Ala Glu Gly Asn Asp Val Tyr Ala
            115             120             125 cct ttt aac tct ctg ttg ccc atg gtt agc cca aac gac ttt gtc gtc      432
Pro Phe Asn Ser Leu Leu Pro Met Val Ser Pro Asn Asp Phe Val Val
        130             135             140 tct ggt tgg gac atc aat aac gca gat cta tac gaa gct atg cag aga      480
Ser Gly Trp Asp Ile Asn Asn Ala Asp Leu Tyr Glu Ala Met Gln Arg
145             150             155             160 agt cag gtt ctc gaa tat gat ctg caa caa cgc ttg aag gcg aag atg      528
Ser Gln Val Leu Glu Tyr Asp Leu Gln Gln Arg Leu Lys Ala Lys Met
            165             170             175 tcc ttg gtg aag cct ctt cct tcc att tac tac cct gat ttc att gca      576
Ser Leu Val Lys Pro Leu Pro Ser Ile Tyr Tyr Pro Asp Phe Ile Ala
            180             185             190 gct aat caa gat gag aga gcc aat aac tgc atc aat ttg gat gaa aaa      624
Ala Asn Gln Asp Glu Arg Ala Asn Asn Cys Ile Asn Leu Asp Glu Lys
            195             200             205 ggc aac gta acc acg agg ggt aag tgg gcc cat ctg caa cgc atc aga      672
Gly Asn Val Thr Thr Arg Gly Lys Trp Ala His Leu Gln Arg Ile Arg
210             215             220 cgc gat att cag aat ttc aaa gaa gaa aac gcc ctt gat aaa gta atc      720
Arg Asp Ile Gln Asn Phe Lys Glu Glu Asn Ala Leu Asp Lys Val Ile
225             230             235             240 gtt ctt tgg act gca aat act gag agg tac gta gaa gta tct cct ggt      768
Val Leu Trp Thr Ala Asn Thr Glu Arg Tyr Val Glu Val Ser Pro Gly
            245             250             255 gtt aat gac acc atg gaa aac ctc ttg cag tct att aag aat gac cat      816
Val Asn Asp Thr Met Glu Asn Leu Leu Gln Ser Ile Lys Asn Asp His
            260             265             270 gaa gag att gct cct tcc acg atc ttt gca gca gca tct atc ttg gaa      864
Glu Glu Ile Ala Pro Ser Thr Ile Phe Ala Ala Ala Ser Ile Leu Glu
            275             280             285 ggt gtc ccc tat att aat ggt tca ccg cag aat act ttt gtt ccc ggc      912
Gly Val Pro Tyr Ile Asn Gly Ser Pro Gln Asn Thr Phe Val Pro Gly
            290             295             300 ttg gtt cag ctg gct gag cat gag ggt aca ttc att gcg gga gac gat      960
Leu Val Gln Leu Ala Glu His Glu Gly Thr Phe Ile Ala Gly Asp Asp
305             310             315             320 ctc aag tcg gga caa acc aag ttg aag tct gtt ctg gcc cag ttc tta     1008
Leu Lys Ser Gly Gln Thr Lys Leu Lys Ser Val Leu Ala Gln Phe Leu
            325             330             335 gtg gat gca ggt att aaa ccg gtc tcc att gca tcc tat aac cat tta     1056
Val Asp Ala Gly Ile Lys Pro Val Ser Ile Ala Ser Tyr Asn His Leu
            340             345             350 ggc aat aat gac ggt tat aac tta tct gct cca aaa caa ttt agg tct     1104
Gly Asn Asn Asp Gly Tyr Asn Leu Ser Ala Pro Lys Gln Phe Arg Ser
            355             360             365 aag gag att tcc aaa agt tct gtc ata gat gac atc atc gcg tct aat     1152
Lys Glu Ile Ser Lys Ser Ser Val Ile Asp Asp Ile Ile Ala Ser Asn
            370             375             380 gat atc ttg tac aat gat aaa ctg ggt aaa aaa gtt gac cac tgc att     1200
Asp Ile Leu Tyr Asn Asp Lys Leu Gly Lys Lys Val Asp His Cys Ile
385             390             395             400
```

| | | |
|---|---|---|
| gtc att aaa tat atg aag ccc gtc ggg gac tca aaa gtg gca atg gac<br>Val Ile Lys Tyr Met Lys Pro Val Gly Asp Ser Lys Val Ala Met Asp<br>                    405                    410                  415 | 1248 |
| gag tat tac agt gag ttg atg tta ggt ggc cat aac cgg att tcc att<br>Glu Tyr Tyr Ser Glu Leu Met Leu Gly Gly His Asn Arg Ile Ser Ile<br>                    420                    425                  430 | 1296 |
| cac aat gtt tgc gaa gat tct tta ctg gct acg ccc ttg atc atc gat<br>His Asn Val Cys Glu Asp Ser Leu Leu Ala Thr Pro Leu Ile Ile Asp<br>                    435                    440                  445 | 1344 |
| ctt tta gtc atg act gag ttt tgt aca aga gtg tcc tat aag aag gtg<br>Leu Leu Val Met Thr Glu Phe Cys Thr Arg Val Ser Tyr Lys Lys Val<br>        450                    455                    460 | 1392 |
| gac cca gtt aaa gaa gat gct ggc aaa ttt gag aac ttt tat cca gtt<br>Asp Pro Val Lys Glu Asp Ala Gly Lys Phe Glu Asn Phe Tyr Pro Val<br>465                    470                    475                  480 | 1440 |
| tta acc ttc ttg agt tac tgg tta aaa gct cca tta aca aga cca gga<br>Leu Thr Phe Leu Ser Tyr Trp Leu Lys Ala Pro Leu Thr Arg Pro Gly<br>                    485                    490                  495 | 1488 |
| ttt cac ccg gtg aat ggc tta aac aag caa aga acc gcc tta gaa aat<br>Phe His Pro Val Asn Gly Leu Asn Lys Gln Arg Thr Ala Leu Glu Asn<br>                    500                    505                  510 | 1536 |
| ttt tta aga ttg ttg att gga ttg cct tct caa aac gaa cta aga ttc<br>Phe Leu Arg Leu Leu Ile Gly Leu Pro Ser Gln Asn Glu Leu Arg Phe<br>        515                    520                    525 | 1584 |
| gaa gag aga ttg ttg taa<br>Glu Glu Arg Leu Leu<br>        530 | 1602 |

```
<210> SEQ ID NO 2
<211> LENGTH: 533
<212> TYPE: PRT
<213> ORGANISM: Saccharomyces cerevisiae

<400> SEQUENCE: 2
```

Met Thr Glu Asp Asn Ile Ala Pro Ile Thr Ser Val Lys Val Val Thr
1               5                   10                  15

Asp Lys Cys Thr Tyr Lys Asp Asn Glu Leu Leu Thr Lys Tyr Ser Tyr
                20                  25                  30

Glu Asn Ala Val Val Thr Lys Thr Ala Ser Gly Arg Phe Asp Val Thr
            35                  40                  45

Pro Thr Val Gln Asp Tyr Val Phe Lys Leu Asp Leu Lys Lys Pro Glu
        50                  55                  60

Lys Leu Gly Ile Met Leu Ile Gly Leu Gly Gly Asn Asn Gly Ser Thr
65                  70                  75                  80

Leu Val Ala Ser Val Leu Ala Asn Lys His Asn Val Glu Phe Gln Thr
                85                  90                  95

Lys Glu Gly Val Lys Gln Pro Asn Tyr Phe Gly Ser Met Thr Gln Cys
            100                 105                 110

Ser Thr Leu Lys Leu Gly Val Asp Ala Glu Gly Asn Asp Val Tyr Ala
        115                 120                 125

Pro Phe Asn Ser Leu Leu Pro Met Val Ser Pro Asn Asp Phe Val Val
    130                 135                 140

Ser Gly Trp Asp Ile Asn Asn Ala Asp Leu Tyr Glu Ala Met Gln Arg
145                 150                 155                 160

Ser Gln Val Leu Glu Tyr Asp Leu Gln Gln Arg Leu Lys Ala Lys Met
                165                 170                 175

Ser Leu Val Lys Pro Leu Pro Ser Ile Tyr Tyr Pro Asp Phe Ile Ala
            180                 185                 190

```
Ala Asn Gln Asp Glu Arg Ala Asn Asn Cys Ile Asn Leu Asp Glu Lys
        195                 200                 205
Gly Asn Val Thr Thr Arg Gly Lys Trp Ala His Leu Gln Arg Ile Arg
    210                 215                 220
Arg Asp Ile Gln Asn Phe Lys Glu Asn Ala Leu Asp Lys Val Ile
225                 230                 235                 240
Val Leu Trp Thr Ala Asn Thr Glu Arg Tyr Val Glu Val Ser Pro Gly
                245                 250                 255
Val Asn Asp Thr Met Glu Asn Leu Leu Gln Ser Ile Lys Asn Asp His
            260                 265                 270
Glu Glu Ile Ala Pro Ser Thr Ile Phe Ala Ala Ser Ile Leu Glu
        275                 280                 285
Gly Val Pro Tyr Ile Asn Gly Ser Pro Gln Asn Thr Phe Val Pro Gly
    290                 295                 300
Leu Val Gln Leu Ala Glu His Glu Gly Thr Phe Ile Ala Gly Asp Asp
305                 310                 315                 320
Leu Lys Ser Gly Gln Thr Lys Leu Lys Ser Val Leu Ala Gln Phe Leu
                325                 330                 335
Val Asp Ala Gly Ile Lys Pro Val Ser Ile Ala Ser Tyr Asn His Leu
            340                 345                 350
Gly Asn Asn Asp Gly Tyr Asn Leu Ser Ala Pro Lys Gln Phe Arg Ser
        355                 360                 365
Lys Glu Ile Ser Lys Ser Ser Val Ile Asp Asp Ile Ile Ala Ser Asn
    370                 375                 380
Asp Ile Leu Tyr Asn Asp Lys Leu Gly Lys Lys Val Asp His Cys Ile
385                 390                 395                 400
Val Ile Lys Tyr Met Lys Pro Val Gly Asp Ser Lys Val Ala Met Asp
                405                 410                 415
Glu Tyr Tyr Ser Glu Leu Met Leu Gly Gly His Asn Arg Ile Ser Ile
            420                 425                 430
His Asn Val Cys Glu Asp Ser Leu Leu Ala Thr Pro Leu Ile Ile Asp
        435                 440                 445
Leu Leu Val Met Thr Glu Phe Cys Thr Arg Val Ser Tyr Lys Lys Val
    450                 455                 460
Asp Pro Val Lys Glu Asp Ala Gly Lys Phe Glu Asn Phe Tyr Pro Val
465                 470                 475                 480
Leu Thr Phe Leu Ser Tyr Trp Leu Lys Ala Pro Leu Thr Arg Pro Gly
                485                 490                 495
Phe His Pro Val Asn Gly Leu Asn Lys Gln Arg Thr Ala Leu Glu Asn
            500                 505                 510
Phe Leu Arg Leu Leu Ile Gly Leu Pro Ser Gln Asn Glu Leu Arg Phe
        515                 520                 525
Glu Glu Arg Leu Leu
    530

<210> SEQ ID NO 3
<211> LENGTH: 804
<212> TYPE: DNA
<213> ORGANISM: Escherichia coli
<220> FEATURE:
<221> NAME/KEY: CDS
<222> LOCATION: (1)..(804)

<400> SEQUENCE: 3 atg cat ccg atg ctg aac atc gcc gtg cgc gca gcg cgc aag gcg ggt        48
```

```
Met His Pro Met Leu Asn Ile Ala Val Arg Ala Ala Arg Lys Ala Gly
1               5                   10                  15 aat tta att gcc aaa aac tat gaa acc ccg gac gct gta gaa gcg agc     96
Asn Leu Ile Ala Lys Asn Tyr Glu Thr Pro Asp Ala Val Glu Ala Ser
            20                  25                  30 cag aaa ggc agt aac gat ttc gtg acc aac gta gat aaa gct gcc gaa    144
Gln Lys Gly Ser Asn Asp Phe Val Thr Asn Val Asp Lys Ala Ala Glu
        35                  40                  45 gcg gtg att atc gac acg att cgt aaa tct tac cca cag cac acc atc    192
Ala Val Ile Ile Asp Thr Ile Arg Lys Ser Tyr Pro Gln His Thr Ile
    50                  55                  60 atc acc gaa gaa agc ggt gaa ctt gaa ggt act gat cag gat gtt caa    240
Ile Thr Glu Glu Ser Gly Glu Leu Glu Gly Thr Asp Gln Asp Val Gln
65                  70                  75                  80 tgg gtt atc gat cca ctg gat ggc act acc aac ttt atc aaa cgt ctg    288
Trp Val Ile Asp Pro Leu Asp Gly Thr Thr Asn Phe Ile Lys Arg Leu
                85                  90                  95 ccg cac ttc gcg gta tct atc gct gtt cgt atc aaa ggc cgc acc gaa    336
Pro His Phe Ala Val Ser Ile Ala Val Arg Ile Lys Gly Arg Thr Glu
            100                 105                 110 gtt gct gtg gta tac gat cct atg cgt aac gaa ctg ttc acc gcc act    384
Val Ala Val Val Tyr Asp Pro Met Arg Asn Glu Leu Phe Thr Ala Thr
        115                 120                 125 cgc ggt cag ggc gca cag ctg aac ggc tac cga ctg cgc ggc agc acc    432
Arg Gly Gln Gly Ala Gln Leu Asn Gly Tyr Arg Leu Arg Gly Ser Thr
    130                 135                 140 gct cgc gat ctc gac ggt act att ctg gcg acc ggc ttc ccg ttc aaa    480
Ala Arg Asp Leu Asp Gly Thr Ile Leu Ala Thr Gly Phe Pro Phe Lys
145                 150                 155                 160 gca aaa cag tac gcc act acc tac atc aac atc gtc ggc aaa ctg ttc    528
Ala Lys Gln Tyr Ala Thr Thr Tyr Ile Asn Ile Val Gly Lys Leu Phe
                165                 170                 175 aac gaa tgt gca gac ttc cgt cgt acc ggt tct gcg gcg ctg gat ctg    576
Asn Glu Cys Ala Asp Phe Arg Arg Thr Gly Ser Ala Ala Leu Asp Leu
            180                 185                 190 gct tac gtc gct gcg ggt cgt gtt gac ggt ttc ttt gaa atc ggt ctg    624
Ala Tyr Val Ala Ala Gly Arg Val Asp Gly Phe Phe Glu Ile Gly Leu
        195                 200                 205 cgc ccg tgg gac ttc gcc gca ggc gag ctg ctg gtt cgt gaa gcg ggc    672
Arg Pro Trp Asp Phe Ala Ala Gly Glu Leu Leu Val Arg Glu Ala Gly
    210                 215                 220 ggc atc gtc agc gac ttc acc ggt ggt cat aac tac atg ctg acc ggt    720
Gly Ile Val Ser Asp Phe Thr Gly Gly His Asn Tyr Met Leu Thr Gly
225                 230                 235                 240 aac atc gtt gct ggt aac ccg cgc gtt gtt aaa gcc atg ctg gcg aac    768
Asn Ile Val Ala Gly Asn Pro Arg Val Val Lys Ala Met Leu Ala Asn
                245                 250                 255 atg cgt gac gag tta agc gac gct ctg aag cgt taa                    804
Met Arg Asp Glu Leu Ser Asp Ala Leu Lys Arg
            260                 265

<210> SEQ ID NO 4
<211> LENGTH: 267
<212> TYPE: PRT
<213> ORGANISM: Escherichia coli

<400> SEQUENCE: 4
```

```
Met His Pro Met Leu Asn Ile Ala Val Arg Ala Ala Arg Lys Ala Gly
1               5                   10                  15

Asn Leu Ile Ala Lys Asn Tyr Glu Thr Pro Asp Ala Val Glu Ala Ser
            20                  25                  30

Gln Lys Gly Ser Asn Asp Phe Val Thr Asn Val Asp Lys Ala Ala Glu
        35                  40                  45

Ala Val Ile Ile Asp Thr Ile Arg Lys Ser Tyr Pro Gln His Thr Ile
    50                  55                  60

Ile Thr Glu Glu Ser Gly Glu Leu Glu Gly Thr Asp Gln Asp Val Gln
65                  70                  75                  80

Trp Val Ile Asp Pro Leu Asp Gly Thr Thr Asn Phe Ile Lys Arg Leu
                85                  90                  95

Pro His Phe Ala Val Ser Ile Ala Val Arg Ile Lys Gly Arg Thr Glu
            100                 105                 110

Val Ala Val Val Tyr Asp Pro Met Arg Asn Glu Leu Phe Thr Ala Thr
        115                 120                 125

Arg Gly Gln Gly Ala Gln Leu Asn Gly Tyr Arg Leu Arg Gly Ser Thr
    130                 135                 140

Ala Arg Asp Leu Asp Gly Thr Ile Leu Ala Thr Gly Phe Pro Phe Lys
145                 150                 155                 160

Ala Lys Gln Tyr Ala Thr Thr Tyr Ile Asn Ile Val Gly Lys Leu Phe
                165                 170                 175

Asn Glu Cys Ala Asp Phe Arg Arg Thr Gly Ser Ala Ala Leu Asp Leu
            180                 185                 190

Ala Tyr Val Ala Ala Gly Arg Val Asp Gly Phe Phe Glu Ile Gly Leu
        195                 200                 205

Arg Pro Trp Asp Phe Ala Ala Gly Glu Leu Leu Val Arg Glu Ala Gly
    210                 215                 220

Gly Ile Val Ser Asp Phe Thr Gly Gly His Asn Tyr Met Leu Thr Gly
225                 230                 235                 240

Asn Ile Val Ala Gly Asn Pro Arg Val Val Lys Ala Met Leu Ala Asn
                245                 250                 255

Met Arg Asp Glu Leu Ser Asp Ala Leu Lys Arg
            260                 265

<210> SEQ ID NO 5
<211> LENGTH: 18
<212> TYPE: DNA
<213> ORGANISM: Artificial Sequence
<220> FEATURE:
<223> OTHER INFORMATION: Forward PCR Primer for suhB Coding Region

<400> SEQUENCE: 5
atgcatccga tgctgaac                                                    18

<210> SEQ ID NO 6
<211> LENGTH: 19
<212> TYPE: DNA
<213> ORGANISM: Artificial Sequence
<220> FEATURE:
<223> OTHER INFORMATION: Reverse PCR Primer for suhB Coding Region

<400> SEQUENCE: 6
ttaacgcttc agagcgtcg                                                   19

<210> SEQ ID NO 7
```

```
<211> LENGTH: 109
<212> TYPE: DNA
<213> ORGANISM: Artificial Sequence
<220> FEATURE:
<223> OTHER INFORMATION: Promoter for suhB coding region

<400> SEQUENCE: 7
gtcgtttttc tgcttaggat tttgttattt aaattaagcc tgtaatgcct tgcttccatt    60
gcggataaat cctactttt tattgccttc aaataaattt aaggagttc                109

<210> SEQ ID NO 8
<211> LENGTH: 22
<212> TYPE: DNA
<213> ORGANISM: Artificial Sequence
<220> FEATURE:
<223> OTHER INFORMATION: Forward PCR Primer for INO1 Coding Region

<400> SEQUENCE: 8
atgacagaag ataatattgc tc                                             22

<210> SEQ ID NO 9
<211> LENGTH: 19
<212> TYPE: DNA
<213> ORGANISM: Artificial Sequence
<220> FEATURE:
<223> OTHER INFORMATION: Reverse PCR Primer for INO1 Coding Region

<400> SEQUENCE: 9
ttacaacaat ctctcttcg                                                 19

<210> SEQ ID NO 10
<211> LENGTH: 155
<212> TYPE: DNA
<213> ORGANISM: Artificial Sequence
<220> FEATURE:
<223> OTHER INFORMATION: Promoter for INO1 coding sequence

<400> SEQUENCE: 10
ctcaagccca aaggaagagt gaggcgagtc agtcgcgtaa tgcttaggca caggattgat    60
ttgtcgcaat gattgacacg attccgcttg acgctgcgta aggttttgt aattttacag   120 gcaaccttt attcactaac aaatagctgg tggaa                              155
```